US010723777B2

(12) United States Patent
Chung et al.

(10) Patent No.: US 10,723,777 B2
(45) Date of Patent: *Jul. 28, 2020

(54) PEPTIDE HAVING ANTI-OBESITY AND ANTI-DIABETES EFFICACY AND USE THEREOF

(71) Applicant: CAREGEN CO., LTD., Anyang-si, Gyeonggi-do (KR)

(72) Inventors: Yong Ji Chung, Yongin-si (KR); Eun Mi Kim, Yongin-si (KR)

(73) Assignee: CAREGEN CO., LTD., Anyang-si, Gyeonggi-Do (KR)

(*) Notice: Subject to any disclaimer, the term of this patent is extended or adjusted under 35 U.S.C. 154(b) by 0 days.
This patent is subject to a terminal disclaimer.

(21) Appl. No.: 16/343,559

(22) PCT Filed: Mar. 29, 2017

(86) PCT No.: PCT/KR2017/003448
§ 371 (c)(1),
(2) Date: Apr. 19, 2019

(87) PCT Pub. No.: WO2018/074682
PCT Pub. Date: Apr. 26, 2018

(65) Prior Publication Data
US 2020/0048323 A1    Feb. 13, 2020

(30) Foreign Application Priority Data
Oct. 19, 2016 (KR) .................. 10-2016-0135615

(51) Int. Cl.
| | |
|---|---|
| A61K 38/08 | (2019.01) |
| A61K 38/00 | (2006.01) |
| A61K 38/30 | (2006.01) |
| A61P 3/00 | (2006.01) |
| A61P 3/04 | (2006.01) |
| A61P 3/06 | (2006.01) |
| A61P 3/10 | (2006.01) |
| C07K 7/06 | (2006.01) |
| C07K 14/575 | (2006.01) |

(52) U.S. Cl.
CPC ............ *C07K 14/5759* (2013.01); *A61P 3/04* (2018.01); *A61P 3/10* (2018.01); *C07K 7/06* (2013.01); *A61K 38/00* (2013.01)

(58) Field of Classification Search
CPC .... A61K 38/00; A61K 38/08; A61K 38/2264; A61K 38/30; A61P 3/00; A61P 3/04; A61P 3/06; A61P 3/10; C07K 7/06
USPC .................. 530/328, 300; 514/21.3, 6.9, 1.1
See application file for complete search history.

(56) References Cited

U.S. PATENT DOCUMENTS

| | | | |
|---|---|---|---|
| 5,516,891 A | 5/1996 | Siwruk et al. | |
| 7,430,476 B2 | 9/2008 | Carr et al. | |
| 9,593,156 B2 | 3/2017 | Dimarchi et al. | |
| 9,637,519 B2 | 5/2017 | Chung et al. | |
| 10,351,597 B2 | 7/2019 | Chung et al. | |
| 2004/0180386 A1 | 9/2004 | Carr et al. | |
| 2005/0288223 A1 | 12/2005 | Lucas et al. | |
| 2007/0060512 A1 | 3/2007 | Sadeghi et al. | |
| 2007/0185025 A1 | 8/2007 | Palacios et al. | |
| 2010/0235935 A1 | 9/2010 | Liu | |
| 2015/0183834 A1 | 7/2015 | Lipkin et al. | |
| 2015/0274802 A1 | 10/2015 | Dimarchi et al. | |
| 2016/0075739 A1 | 3/2016 | Chung et al. | |
| 2018/0118783 A1* | 5/2018 | Chung ................... | A61K 38/30 |
| 2019/0270772 A1 | 9/2019 | Chung et al. | |
| 2019/0270773 A1 | 9/2019 | Chung et al. | |
| 2019/0270774 A1 | 9/2019 | Chung et al. | |

FOREIGN PATENT DOCUMENTS

| | | |
|---|---|---|
| EP | 1366455 B1 | 12/2003 |
| EP | 2998313 A1 | 3/2016 |
| EP | 3290434 A1 | 7/2018 |
| KR | 10-2013-0086339 A | 8/2013 |
| KR | 10-214-0027594 A | 3/2014 |
| KR | 10-2014-0134083 A | 11/2014 |
| KR | 10-2015-0031413 A | 3/2015 |
| KR | 10-1669140 B1 | 10/2016 |
| WO | 02/069232 A2 | 9/2002 |
| WO | 03/097689 A1 | 11/2003 |
| WO | 2014/052451 A2 | 4/2014 |

(Continued)

OTHER PUBLICATIONS

International Search Report and Written Opinion from International Application No. PCT/KR2017/003448, dated Aug. 1, 2017.
R. B. Merrifield: "Solid Phase Peptide Synthesis. I. The Synthesis of a Tetrapeptide," Synthesoifs a Tetrapeptide, vol. 85, pp. 2149-2154 (Jul. 20, 1963).
Extended European Search Report from European Application No. 17861361.8, dated Oct. 28, 2019.

(Continued)

*Primary Examiner* — Julie Ha
(74) *Attorney, Agent, or Firm* — Merchant & Gould P.C.

(57) ABSTRACT

The present disclosure relates to peptides exhibiting an anti-obesity effect by inhibiting fat accumulation and decomposing already accumulated fats as well as an outstanding anti-diabetes effect by effectively lowering blood sugar levels. The peptides that downregulate the expression of the adipogenic markers PPARγ, ACC and/or aP2, upregulate the expression of the lipolytic factors pHSL, AMPK-α1, CGI-58 and/or ATGL, and reduce sizes of adipocyte and levels of cholesterol in blood are described. The excellent activity and stability of the peptides described herein provides advantages in applications such as drugs and quasi-drug products.

15 Claims, 40 Drawing Sheets

Specification includes a Sequence Listing.

(56) References Cited

FOREIGN PATENT DOCUMENTS

WO      2016/011133 A1      1/2016
WO      2016/175362 A1      11/2016

OTHER PUBLICATIONS

First Office Action from Russian Application No. 2019115134/04(028842), dated Nov. 19, 2019.
Hideotoshi et al.: "Identification of amino-terminal region of adiponectin as a physiologically functional domain", Journal of Cellular Biochemistry, A.R. Liss, vol. 98, No. 1, Jan. 11, 2006 (Jan. 11, 2006), pp. 194-207, XP002476528.

* cited by examiner

PEPTIDE HAVING ANTI-OBESITY AND ANTI-DIABETES EFFICACY AND USE THEREOF

This application is a National Stage Application of PCT/KR2017/003448, filed 29 Mar. 2017, which claims benefit of Serial No. 10-2016-0135615, filed 19 Oct. 2016 in the Republic of Korea and which applications are incorporated herein by reference. To the extent appropriate, a claim of priority is made to each of the above disclosed applications.

TECHNICAL FIELD

The prevent invention relates to a peptide having anti-obesity and anti-diabetic efficacy and use thereof.

BACKGROUND

In Korea, dietary fat intake has recently increased with the growth of economy and the westernization of diet life, and onset of metabolic diseases such as obesity, diabetes, hyperlipidemia, hypertension, arteriosclerosis, and fatty liver are increasing due to insufficient exercise. In addition, obesity not only hurts the beauty of younger people who likes slim body shape, but also is associated with various disorders as obesity continues.

At present, therapeutic agents for obesity may be broadly classified into drugs that act on the central nervous system to affect appetite, and drugs that act on the gastrointestinal tract to inhibit uptake. Drugs acting on the central nervous system are commercially available as anti-obesity drugs which inhibit the serotonergic (5-HT) nervous system such as fenfluramine and dexfenfluramine, act through the noradrenergic nervous system such as ephedrine and caffeine, and act on both the serotonergic and the noradrenergic nervous systems such as recently developed sibutramine, according to their respective mechanisms. In addition, representative anti-obesity drugs acting on the gastrointestinal tract are orlistat, etc., approved as a therapeutic agent for obesity, which inhibits intestinal lipase to reduce fat uptake.

However, there are problems with some of the existing drugs. For example, drugs such as fenfluramine have been recently prohibited from being marketed due to the side effect of incurring primary pulmonary hypertension or valvular heart disease, and other drugs cannot be also used to patients suffering from heart failure or kidney disease due to the occurrence of decreased blood pressure or lactic acidosis.

Diabetes is a type of metabolic disorder caused when insulin is insufficiently secreted or normal function is not achieved (DeFronzo, 1988), and is characterized by hyperglycemia with high blood glucose levels, which causes a variety of symptoms and signs and makes glucose excreted into urine. Recently, the incidence of diabetes has explosively increasing due to the increase in obesity rate, especially abdominal obesity.

The number of diabetic patients was estimated to be 170 million worldwide in 2000 and expected to reach 370 million in 2030. However, it has recently been reported that the number of diabetic patients already reached 350 million worldwide in 2008, which is far worse than expected (Danaei et al., 2011). It is reported that more than about 80% of type 2 diabetic patients are obese, while only less than 10% of obese patients have diabetes (Harris et al. 1987).

The relationship between diabetes and obesity is attributed to the fact that adipokines and free fatty acids are irregularly secreted to cause fatty acids to accumulate in insulin-sensitive tissues such as the beta cells, kidneys, liver, heart, etc., resulting in lipotoxicity. If chronic hyperglycemia is not treated properly, it is accompanied by various pathological symptoms such as retinopathy, renal dysfunction, neuropathy, and vascular disorder in the body. Effective management of blood sugar levels is essential to prevent such complications.

Currently, the method of controlling blood sugar levels is accomplished by lifestyle improvement (for example, diet therapy and exercise therapy), drug therapy, etc. However, diet therapy or exercise therapy is difficult to strictly manage and implement, and there are limitations in its effects. Thus, most of diabetic patients rely on the control of blood sugar levels by drugs such as insulin, insulin secretagogues, insulin sensitizers, and hypoglycemic agents, as well as lifestyle improvement.

Insulin produced by a recombinant method is an essential drug for type 1 diabetic patients and type 2 diabetic patients which fail to control blood sugar levels, and is advantageous in the control of blood sugar levels. However, it has the disadvantages such as repulsion to injection needles, difficulty in administration method, risk of hypoglycemia, and weight gain.

Meglitinides, a kind of insulin secretagogues, are very short-acting agents which are taken before meals, and include NovoNorm (repaglinide), Fastic (nateglinide), Glufast (mitiglinide), and the like. Insulin sensitizers are characterized by causing little hypoglycemia when taken alone, and include biguanide drugs such as metformin, thiazolidinedione drugs such as Avanida (rosiglitazone) and Actos (pioglitazone), and the like.

Recently, GLP-1 agonists have been developed using the action of glucagon-like peptide-1, a hormone that promotes insulin secretion, and include exenatide and Victoza (liraglutide). In addition, dipeptidyl peptidase-4 (DDP-4) inhibitors that inhibit the action of DPP-4, an enzyme that rapidly inactivates GLP-1, are recently developed drugs, and are representatively exemplified by Januvia (ingredient name: sitagliptin).

However, these drugs have been reported to have side effects such as hepatoxicity, gastrointestinal disorders, cardiovascular diseases, and carcinogenicity. The annual cost of treatment with these drugs is also high, thereby making it a barrier to the treatment of diabetes. Indeed, health care costs of pre-diabetes and diabetes are close to about KRW 200 trillion in the US in 2007 (Dall et al., 2010), and health care costs of obesity are also approaching about KRW 150 trillion in the US in 2008 (Finkelstein et al., 2009). Therefore, there is an urgent need for the development of a drug which can effectively lower blood sugar levels to be applied to the treatment of both diabetes and obese type diabetes, while having few side effects.

DISCLOSURE

Technical Problem

For this, the present inventors have recently paid attention to energy metabolism-regulating mechanisms in order to find an improved method for treating obesity, and have conducted research on signals responsible for fat accumulation and proteins affecting fat accumulation upon the intake of high-fat diets in humans, assuming that the compound to be developed should have higher safety (lower toxicity). As a result of research on signals for suppressing the expression of proteins responsible for fat accumulation and for decomposing already accumulated fats and on proteins involved in the signaling, the present inventors have succeeded in developing peptides that promote lipolysis.

Accordingly, an object of the present invention is to provide a peptide consisting of the amino acid sequence of SEQ ID NO: 2 or SEQ ID NO: 4.

Another object of the present invention is to provide a peptide consisting of the amino acid sequence of SEQ ID NO: 2 or SEQ ID NO: 4, having anti-obesity or anti-diabetic activity.

A further object of the present invention is to provide a pharmaceutical composition for preventing and/or treating obesity, comprising one or more peptides selected from the group consisting of the peptide consisting of the amino acid sequence of SEQ ID NO: 2 or SEQ ID NO: 4.

A still further object of the present invention is to provide a pharmaceutical composition for preventing and/or treating diabetes, comprising one or more peptides selected from the group consisting of the peptide consisting of the amino acid sequence of SEQ ID NO: 2 or SEQ ID NO: 4.

Technical Solution

As a result of efforts to develop a number of excellent peptides having a biologically effective activity, the present inventors have completed the present invention on the basis of the finding that peptides consisting of the amino acid sequences selected from the group consisting of SEQ ID NO: 1 to SEQ ID NO: 7 exhibits an anti-obesity effect by inhibiting fat accumulation by high-fat diets and decomposing already accumulated fats, as well as outstanding prophylactic and/or therapeutic effects on diabetes, obese type diabetes, and diabetic complications.

Hereinafter, the present invention will be described in more detail.

An embodiment of the present invention relates to a peptide consisting of the amino acid sequence of SEQ ID NO: 2 or SEQ ID NO: 4.

Another embodiment of the present invention relates to a peptide consisting of the amino acid sequence of SEQ ID NO: 2 or SEQ ID NO: 4, having anti-obesity and/or anti-diabetic activity.

The peptides of the present invention may be modified at N-terminal and/or C-terminal thereof in order to select some regions of the amino acid sequences thereof and increase the activity thereof. Through such N-terminal and/or C-terminal modifications, the stability of the peptides of the present invention may be significantly improved and, for example, the half-life of the peptide after in vivo administration may be increased.

The N-terminal modification may be carried out by coupling the peptides with a protecting group selected from the group consisting of an acetyl group, a fluorenylmethoxycarbonyl group, a formyl group, a palmitoyl group, a myristyl group, a stearyl group, and a polyethylene glycol (PEG) at N-terminal. The protecting group acts to protect the peptides of the present invention against the attack of a protein cleaving enzyme in vivo.

The C-terminal modification may be carried out by coupling the peptides with a hydroxyl group (—OH), an amino group (—NH$_2$), an azide group (—NHNH$_2$), or the like, at C-terminal.

According to an embodiment of the present invention, a peptide consisting of the amino acid sequence of SEQ ID NO: 2 or SEQ ID NO: 4 exhibits the effect of inhibiting fat accumulation by high-fat diets and decomposing already accumulated fats.

The peptide downregulates the expression of the adipogenic markers peroxisome proliferator-activated receptor gamma (PPARγ), acetyl-CoA carboxylase (ACC), and/or adipose-specific fatty acid-binding protein 2 (aP2).

The peptide upregulates the expression of the lipolytic factors phospho-hormone-sensitive lipase (pHSL), AMP-activated protein kinase al (AMPK-α1), comparative gene identification-58 (CGI-58), and/or adipose triglyceride lipase (ATGL). The peptide reduces sizes of adipocytes.

In addition, the peptide has the effects of increasing lipolysis, inhibiting adipogenesis, lowering blood sugar levels, reducing sizes of adipocytes, and lowering levels of cholesterol in blood.

These results indicate that the peptides of the present invention have very excellent efficacy in the treatment of obesity, diabetes, and obese type diabetes.

According to the present invention, the peptide consisting of the amino acid sequence of SEQ ID NO: 2 or SEQ ID NO: 4 corresponds respectively to that consisting of the amino acid sequence of SEQ ID NO: 3 or SEQ ID NO: 5, with the exception that the Ser residue is substituted with the Cys residue. The corresponding paired peptides are almost identical in terms of anti-obesity and/or anti-diabetic activities.

Another embodiment of the present invention relates to a peptide complex having anti-obesity and/or anti-diabetic activities, comprising two or more peptides consisting of the amino acid sequence selected from the group consisting of SEQ ID NO: 1 to SEQ ID NO: 7.

The peptide complex comprises one or more peptides consisting of the amino acid sequence selected from the group consisting of SEQ ID NO: 2 and SEQ ID NO: 4, and may further comprise one or more peptides consisting of the amino acid sequence selected from the group consisting of SEQ ID NO: 1, SEQ ID NO: 3, SEQ ID NO: 5, SEQ ID NO: 6, and SEQ ID NO: 7.

For example, the peptide complex may be a combination of the following peptides:
(a) a peptide consisting of the amino acid sequence of SEQ ID NO: 1;
(b) a peptide consisting of the amino acid sequence of SEQ ID NO: 2 or SEQ ID NO: 3; and
(c) a peptide consisting of the amino acid sequence of SEQ ID NO: 6 or SEQ ID NO: 7.

In addition, the peptide complex may be a combination of the following peptides:
(a) a peptide consisting of the amino acid sequence of SEQ ID NO: 1;
(b) a peptide consisting of the amino acid sequence of SEQ ID NO: 3 or SEQ ID NO: 4; and
(c) a peptide consisting of the amino acid sequence of SEQ ID NO: 6 or SEQ ID NO: 7.

The peptide complexes as well as the peptides consisting of the amino acid sequence selected from the group consisting of SEQ ID NO: 1 to SEQ ID NO: 7 have excellent anti-obesity and/or anti-diabetic activities.

A further embodiment of the present invention relates to a pharmaceutical composition for preventing and/or treating obesity, comprising one or more peptides selected from the group consisting of the peptide consisting of the amino acid sequence of SEQ ID NO: 2 or SEQ ID NO: 4 as an active ingredient.

The peptides are excellent in the functions of inhibiting adipogenesis and decomposing lipids, thereby being able to be used for preventing and/or treating obesity.

The pharmaceutical composition for preventing and/or treating obesity may further comprise one or more peptides selected from the group consisting of the peptide consisting of the amino acid sequence selected from the group consisting of SEQ ID NO: 1, SEQ ID NO: 3, SEQ ID NO: 5, SEQ ID NO: 6, and SEQ ID NO: 7.

A still further embodiment of the present invention relates to a pharmaceutical composition for preventing and/or treating diabetes, comprising one or more peptides selected from the group consisting of the peptide consisting of the amino acid sequence of SEQ ID NO: 2 or SEQ ID NO: 4 as an active ingredient.

The peptides exhibit the efficacy of effectively lowering an elevated blood sugar levels in diabetic animal models, thereby be able to be used for preventing and/or treating diabetes.

The pharmaceutical composition for preventing and/or treating diabetes may further comprise one or more peptides selected from the group consisting of the peptide consisting of the amino acid sequence selected from the group consisting of SEQ ID NO: 1, SEQ ID NO: 3, SEQ ID NO: 5, SEQ ID NO: 6, and SEQ ID NO: 7.

According to preferred embodiments of the present invention, the pharmaceutical composition for preventing or treating obesity or diabetes may comprise: (a) a pharmaceutically effective amount of peptide consisting of the amino acid sequence of SEQ ID NO: 2 or SEQ ID NO: 4; and a pharmaceutically acceptable carrier.

The pharmaceutically acceptable carriers are those commonly used in formulations and include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil.

The pharmaceutical composition of the present invention may further comprise, but not limited to, a lubricant, a humectant, a sweetener, a flavouring agent, an emulsifier, a suspending agent, and a preservative, in addition to the above-mentioned ingredients.

Suitable pharmaceutically acceptable carriers and agents are disclosed in detail in Remington's Pharmaceutical Sciences (19th ed., 1995).

The pharmaceutical composition may be administered orally or parenterally, preferably parenterally. For parenteral administration, it may be administered by, but not limited to, intramuscular injection, intravenous injection, subcutaneous injection, intraperitoneal injection, topical administration, transcutaneous administration, or the like.

The dosage of the pharmaceutical composition to be administered may vary depending on various factors, including dosage form, the mode of administration, the age, body weight, sex, and medical condition of the patient, diet, the time and route of administration, the rate of excretion, sensitivity, etc. For example, the dosage range may be, but is not limited to, from 0.0001 to 1,000 µg per day, from 0.001 to 1000 µg per day, from 0.01 to 1000 µg per day, 0.1 to 1000 µg per day, or 1.0 to 1000 µg per day.

The pharmaceutical composition may be formulated in a single-dose form or in multi-dose packages using a pharmaceutically acceptable carrier and/or excipient, according to a method that may be easily carried out by those skilled in the art.

The formulation may be in the form of a solution, suspension, or emulsion in oil or aqueous medium, or in the form of an extract, a powder, a granule, a tablet, or a capsule, and may further comprise a dispersing agent and/or a stabilizer.

As used herein, the term "peptide" refers to a linear molecule formed by linking amino acid residues with each other by peptide bonds. The peptides of the present invention may be prepared using chemical synthesis methods known in the art, especially solid-phase synthetic techniques (Merrifield, J. Amer. Chem. Soc. 85: 2149-54 (1963); and Stewart, et al., Solid Phase Peptide Synthesis, 2nd. ed., Pierce Chem. Co.: Rockford, 111 (1984)) or liquid-phase synthetic techniques (U.S. Pat. No. 5,516,891).

As used herein, the term "stability" refers to storage stability (e.g., stability during storage at room temperature) as well as stability in vivo.

As used herein, the term "pharmaceutically effective amount" means a sufficient amount to achieve the above-mentioned efficacy or activity of the peptide.

Advantageous Effects

The present invention relates to a peptide having anti-obesity and anti-diabetic efficacy and a composition for preventing or treating obesity or diabetes comprising the same, and the peptide of the present invention exhibits excellent efficacy in diabetes and obese type diabetes. The suppression of insulin signaling attributed to fat accumulation by high-fat diets or fat accumulation in the liver or muscle, and the induced insulin resistance cause diabetes. Therefore, the peptides according to the present invention can be used for the prophylactic or therapeutic use of such diabetes and obese type diabetes.

BEST MODE

Figure 1A:
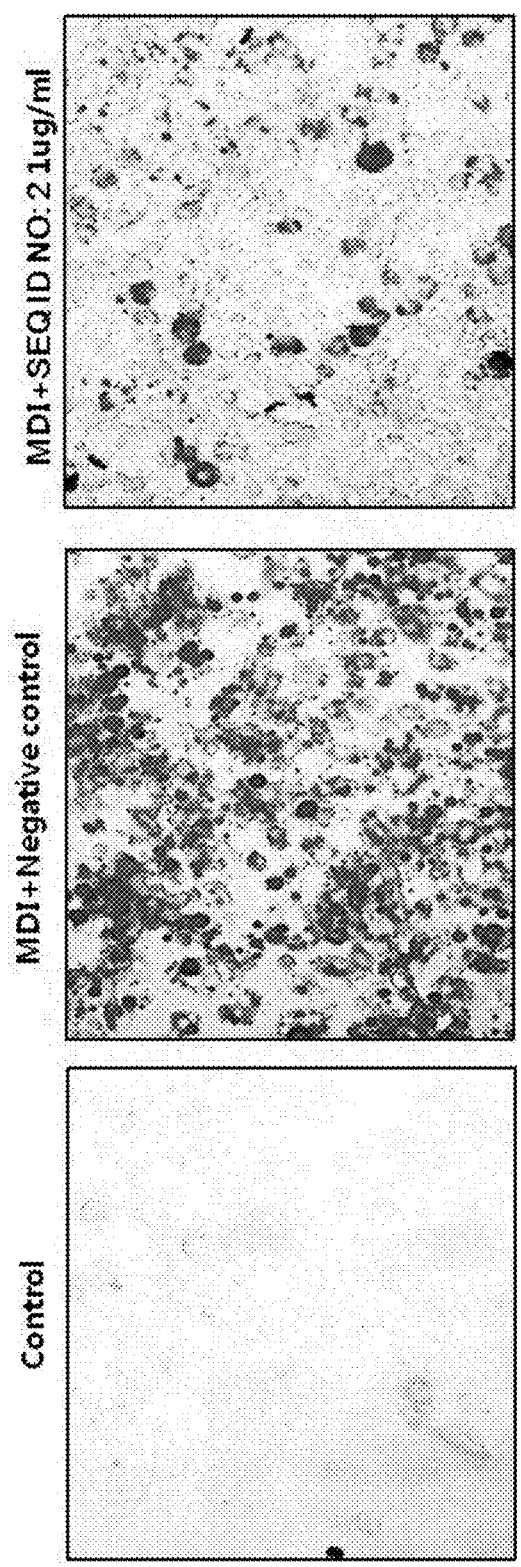
FIG. 1a shows accumulated fats after treatment with the peptide consisting of the amino acid sequence of SEQ ID NO: 2 according to an embodiment of the present invention, as analyzed by Oil Red O staining.

The present invention relates to a peptide consisting of the amino acid sequence of SEQ ID NO: 2 or SEQ ID NO: 4.

Hereinafter, the present invention will be described in more detail with reference to the following examples. However, the examples are only for illustrating the present invention, and are not to be construed to limit the scope of the present invention.

EXAMPLES

Synthesis Example 1: Peptide Synthesis 700 mg of chlorotrityl chloride resins (CTL resins, Nova biochem Cat No. 01-64-0021) was placed in a reactor and 10 ml of methylene chloride (MC) was added thereto, followed by stirring for 3 minutes. After removal of the solution, 10 ml of dimethyl formamide (DMF) was added and stirred for 3 minutes, and then the solvent was removed again. To the reactor, 10 ml of a dichloromethane solution was poured, 200 mmoles of Fmoc-Asn(Trt)-OH (Bachem, Swiss) and 400 mmoles of diisopropyl ethylamine (DIEA) were added thereto and stirred to be thoroughly dissolved, and then reaction was carried out while stirring for 1 hour. After completion of the reaction, washing was performed, and reaction was carried out with a solution of methanol and DIEA (2:1) in DCM (dichloromethane) for 10 minutes, and then washing was performed with an excess of DCM/DMF (1:1). Thereafter, the solution was removed, 10 ml of dimethyl formamide (DMF) was added and stirred for 3 minutes, and then the solvent was removed again. 10 ml of a deprotecting solution (20% piperidine/DMF) was poured into the reactor and stirred at room temperature for 10 minutes, and then the solution was removed. Thereafter, the same amount of deprotecting solution was added to maintain the reaction for 10 minutes again, and then the solution was removed. Thereafter, washing was performed twice with DMF, once with MC, and once with DMF for 3 minutes, respectively to give Asn-CTL resins. In another reactor, 200 mmoles of Fmoc-Arg(Pbf)-OH (Bachem, Swiss), 200 mmoles of HoBt, and 200 mmoles of Bop were added to 10 ml of a DMF solution and well dissolved by stirring. 400 mmoles of DIEA fraction was added over two times to the reactor, and then was stirred for at least 5 minutes until the solid was completely dissolved. The dissolved amino acid mixture solution was poured into the reactor containing the deprotected resins and allowed to react for 1 hour at room temperature while stirring it. After the reaction, the reaction solution was removed by stirring it three times, each for 5 minutes with a DMF solution. A small amount of the reacted resin was taken and used in a Kaiser test (Nihydrin Test) for examining an extent of the reaction. The same deprotection reaction as stated above was performed twice with the deprotecting solution to afford Arg-Asn-CTL resins. The resins were sufficiently washed with DMF and MC, and underwent the Kaiser test once again to perform an amino acid attachment experiments below in the same manner as described above. According to selected amino acid sequences, chain reactions were sequentially performed in the order of Fmoc-Thr(tBu)-OH, Fmoc-Lys(Boc)-OH, and Fmoc-Leu-OH. The Fmoc-protecting group was removed by reacting the reacted amino acid sequence with a deprotecting solution twice, each for 10 minutes and then well washing. Acetic anhydride, DIEA, and HoBt were added and subjected to acetylation for 1 hour. The resulting peptidyl resins were washed with DMF, MC, and methanol three times, respectively. The resins were dried under a slow flow of nitrogen gas and then were completely vacuum-dried under a P2O5 atmosphere. The resins were reacted for 2 hours at room temperature with 30 ml of a leaving solution (trifluoroacetic acid 81.5%, distilled water 5%, thioanisole 5%, phenol 5%, EDT 2.5%, and TIS 1%) while intermittently shaking. The resins were filtered and washed with a small volume of TFA solution, after which the filtrate was combined with the mother liquid. The distillation was carried out under reduced pressure so that the total volume is remained to be half, and then 50 ml of cold ether was added to induce precipitation. The precipitates were collected by centrifugation and washed twice with cold ether. The mother liquid was removed and sufficiently dried under a nitrogen atmosphere to afford 0.85 g of the unpurified peptide of NH$_2$-Leu-Lys-Thr-Arg-Asn-COOH (SEQ ID NO: 1) (yield: 92%). The peptides of 0.78 g of NH$_2$-Lys-Gly-Ala-Cys(Ser)-Thr-Gly-Trp-Met-Ala-COOH (SEQ ID NO: 2) (yield: 82%), 0.92 g of NH$_2$-Ala-Cys(Ser)Thr-Leu-Pro-His-Pro-Trp-Phe-Cys(Ser)-COOH (SEQ ID NO: 3) (yield: 85%), and 0.76 g of NH$_2$—Cys(Ser)-Asp-Leu-Arg-Arg-Leu-Glu-Met-Tyr-Cys(Ser)-COOH (SEQ ID NO: 4) (yield: 88%) were synthesized. The peptides of SEQ ID NOS: 1, 2, and 4 were found to have molecular weights of 630.7 (calculated: 630.7), 924.5 (calculated: 924.1), 1236 (calculated: 1236.5), and 1301.5 (calculated: 1301.5), respectively, as measured by mass spectrometry.

TABLE 1

| SEQ ID NO | Amino Acid Sequence | Analysis (Mass spectrometry) | |
|---|---|---|---|
| | | Measured | Calculated |
| 1 | LKTRN | 630.7 | 630.7 |
| 2 | KGACTGWMA | 924.5 | 924.1 (908.0) |
| 3 | KGASTGWMA | | |
| 4 | ACYLPHPWFC | 1236 | 1236.5 (1269.4) |
| 5 | ASYLPHPWFS | | |
| 6 | CDLRRLEMYC | 1301.5 | 1301.5 |
| 7 | SDLRRLEMYS | | |

On the other hand, each peptide consisting of the amino acid sequences of SEQ ID NO: 1, SEQ ID NO: 3, and SEQ ID NO: 7 was mixed in equal amount to prepare a peptide complex and its efficacy was evaluated.

Example 1: Assay for Inhibitory Activity Against Adipogenesis 1-1. Inhibition of Fat Accumulation Using Pre-Adipocyte (Oil Red O Staining)

The pre-adipocytes 3T3-L1 cells were incubated until becoming confluent, and then incubated for two days after treatment with various concentrations of the peptides in a differentiation medium containing 10 µg/ml insulin, 0.1 µM dexamethasone, and 0.5 µM IBMX. Thereafter, the medium was exchanged every two days to a medium containing 10 µg/ml insulin. After differentiation was induced for 10 days, the generation of droplet in the cells was confirmed by Oil Red 0 staining.

Figure 1B:
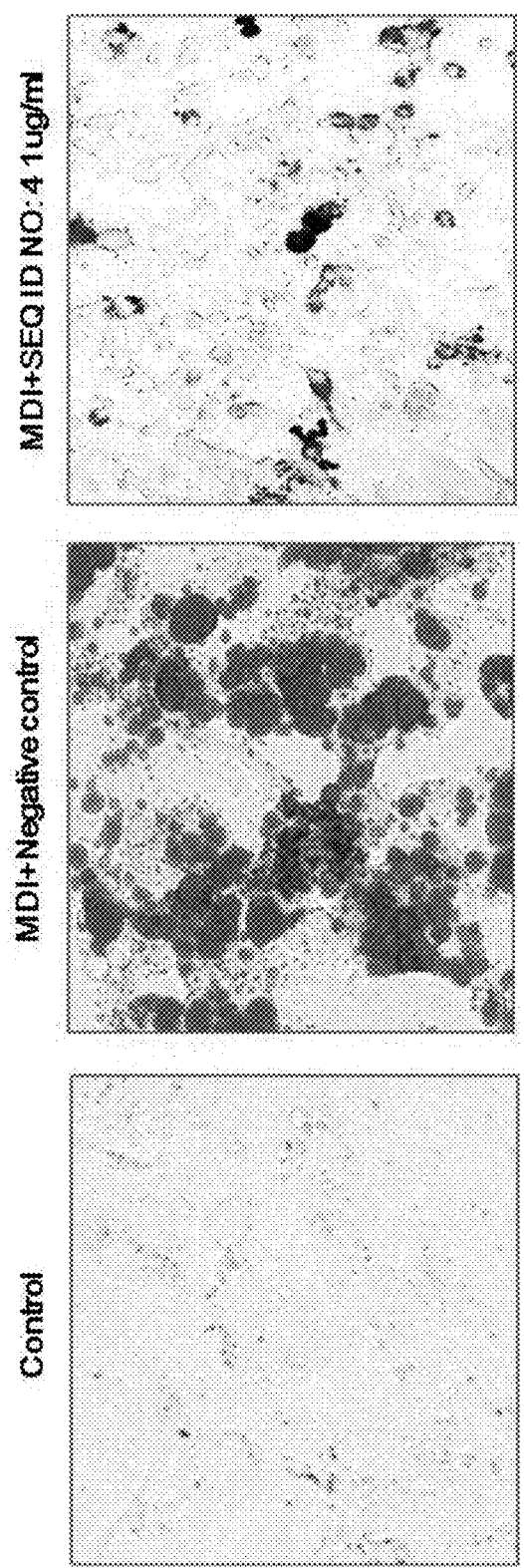
FIG. 1b shows accumulated fats after treatment with the peptide consisting of the amino acid sequence of SEQ ID NO: 4 according to an embodiment of the present invention, as analyzed by Oil Red O staining.

The prepared 3T3-L1 pre-adipocytes were washed with PBS, fixed with 3.7% formalin for 1 hour, were washed with 60% isopropanol, and then were dyed with Oil Red O solution at room temperature for 20 minutes. After completion of dyeing, the Oil Red O solution was removed, the cells were washed three times with distilled water, and then the dyed cells were observed under a phase contrast microscope. The results are shown in FIGS. 1a and 1b. For quantitative analysis, fats were extracted from the cells using 100% isopropanol, and the cells were transferred in an amount of 200 µl/well into 96-well plates and measured for optical density at 500 nm using an ELISA reader. The results are shown in FIG. 2.

As shown in FIGS. 1a and 1b, it was confirmed that the degree of fat accumulation in the cells was decreased after treatment with the peptide consisting of the amino acid sequence of SEQ ID NO: 2 or SEQ ID NO: 4, as measured by Oil Red 0 staining.

Figure 2A:
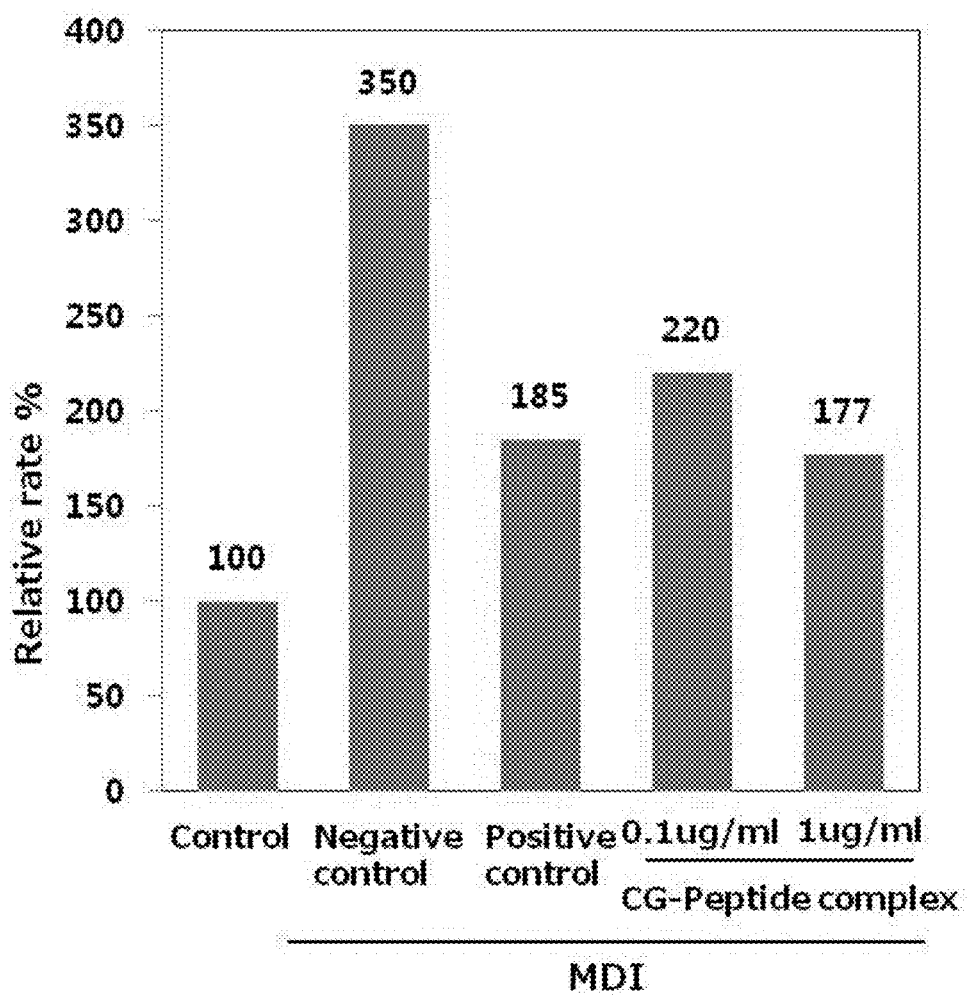
FIG. 2a is a graph showing the results of fat accumulation after treatment with various concentrations of the peptide complexes according to an embodiment of the present invention, as analyzed by Oil Red O staining.
Figure 2B:
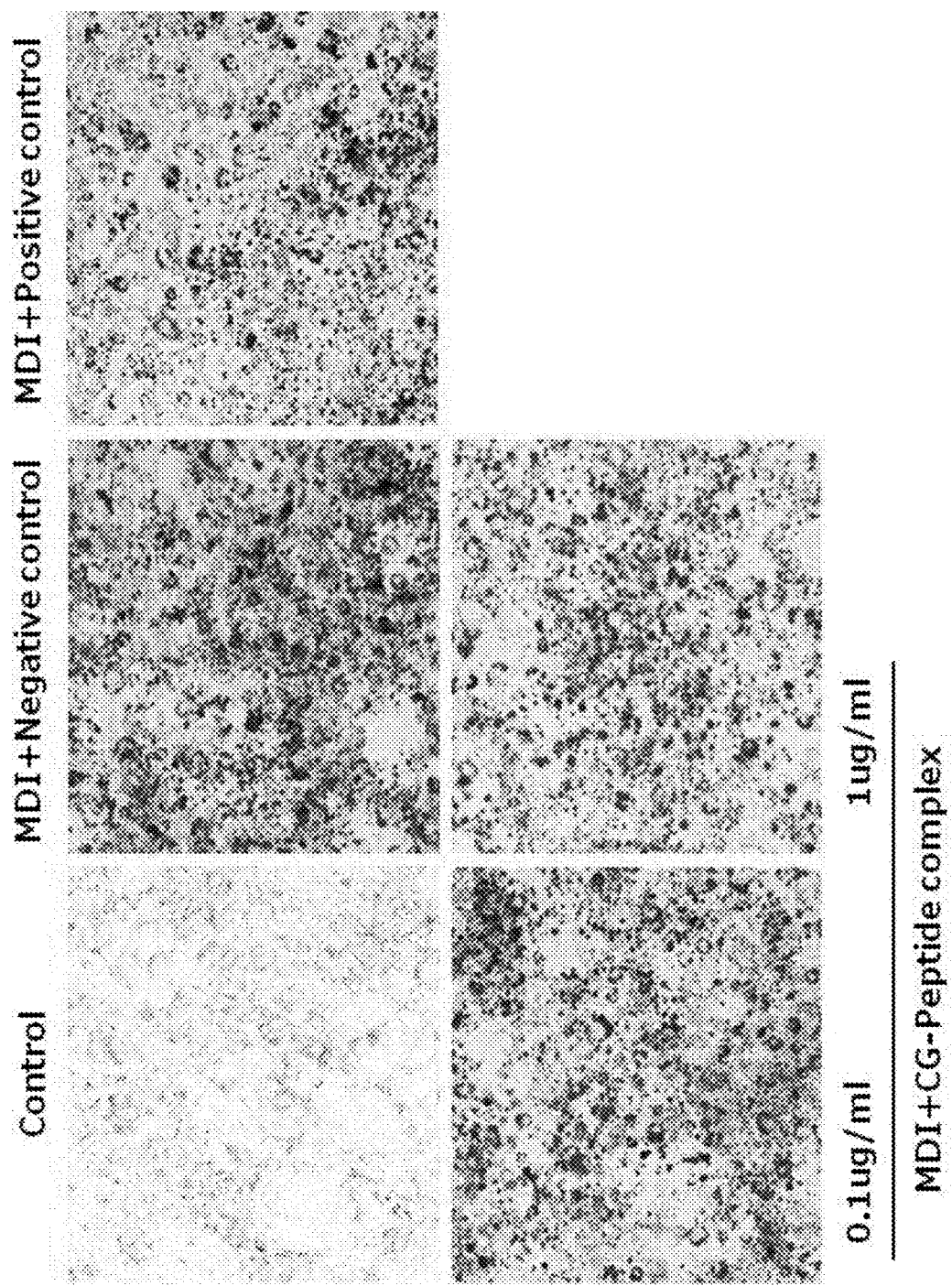
FIG. 2b is a photograph showing the results of fat accumulation after treatment with various concentrations of the peptide complexes according to an embodiment of the present invention, as analyzed by Oil Red O staining.

As shown in FIG. 2, it was confirmed that the degree of fat accumulation in the cells was also decreased after treatment with various concentrations of the peptide complexes.

1-2. Suppression of Expression of Genes Involved in Adipogenesis

3T3-L1 cells (pre-adipocytes) were seeded at a density of 3×10⁵ cells/well into 6-well plates. After incubating for 24 hours, the cells were incubated for 14 days in a 37° C. incubator after treatment with various concentrations (0.1, 1, and 10 µg/ml) of the peptides. Thereafter, the cells were harvested and treated with an RNA extraction solution (Easy Blue, Intron) to prepare for RNA from which cDNA was then synthesized using an RT premix (Intron). PCR was performed using primers for the adipogenic markers (PPARγ, ACC, and aP2), and a PCR premix (Intron). Next, the PCR products were each loaded in an amount of 5 µl into a 1% agarose gel and electrophoresis was performed, and then bands were identified in a Gel-Doc. The results are shown in FIGS. 3a and 3b.

Target-specific primer sequences for PCR of adipogenic markers are as follows:

| SEQ ID NO | Primer | Sequence (5'-3') | Annealing Temperature (° C.) |
|---|---|---|---|
| 8 | PPARγ_F | TTTTCAAGGGTGCCAGTTTC | 60 |
| 9 | PPARγ_R | AATCCTTGGCCCTCTGAGAT | 60 |
| 10 | ACC_F | ACCTTACTGCCATCCCATGTGCTA | 60 |
| 11 | ACC_R | GTGCCTGATGATCGCACGAACAA | 60 |
| 12 | aP2_F | CATCAGCGTAAATGGGGATT | 60 |
| 13 | aP2_R | ACACATTCCACCACCAGCTT | 60 |

Figure 3A:
FIG. 3a shows the measured results of the expression levels of the gene aP2, which is involved in adipogenesis, after treatment with the peptide consisting of the amino acid sequence of SEQ ID NO: 2 according to an embodiment of the present invention.
Figure 3B:
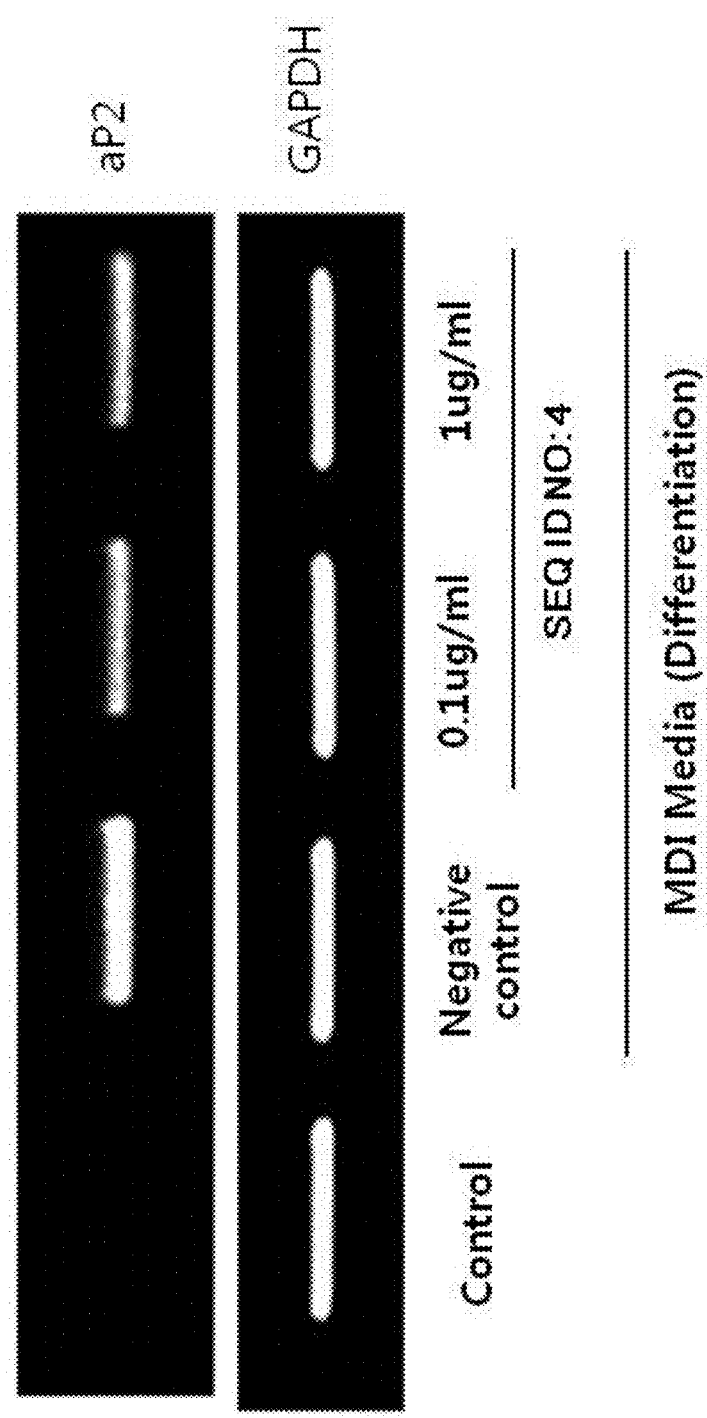
FIG. 3b shows the measured results of the expression levels of the gene aP2, which is involved in adipogenesis, after treatment with the peptide consisting of the amino acid sequence of SEQ ID NO: 4 according to an embodiment of the present invention.

As shown in FIGS. 3a and 3b, it was observed that in the mouse osteoblast cell line 3T3-L1 which was incubated for three days after treatment with the peptide consisting of the amino acid sequence of SEQ ID NO: 2 or SEQ ID NO: 4, the expression levels of the adipogenic marker aP2 were decreased.

Figure 4:
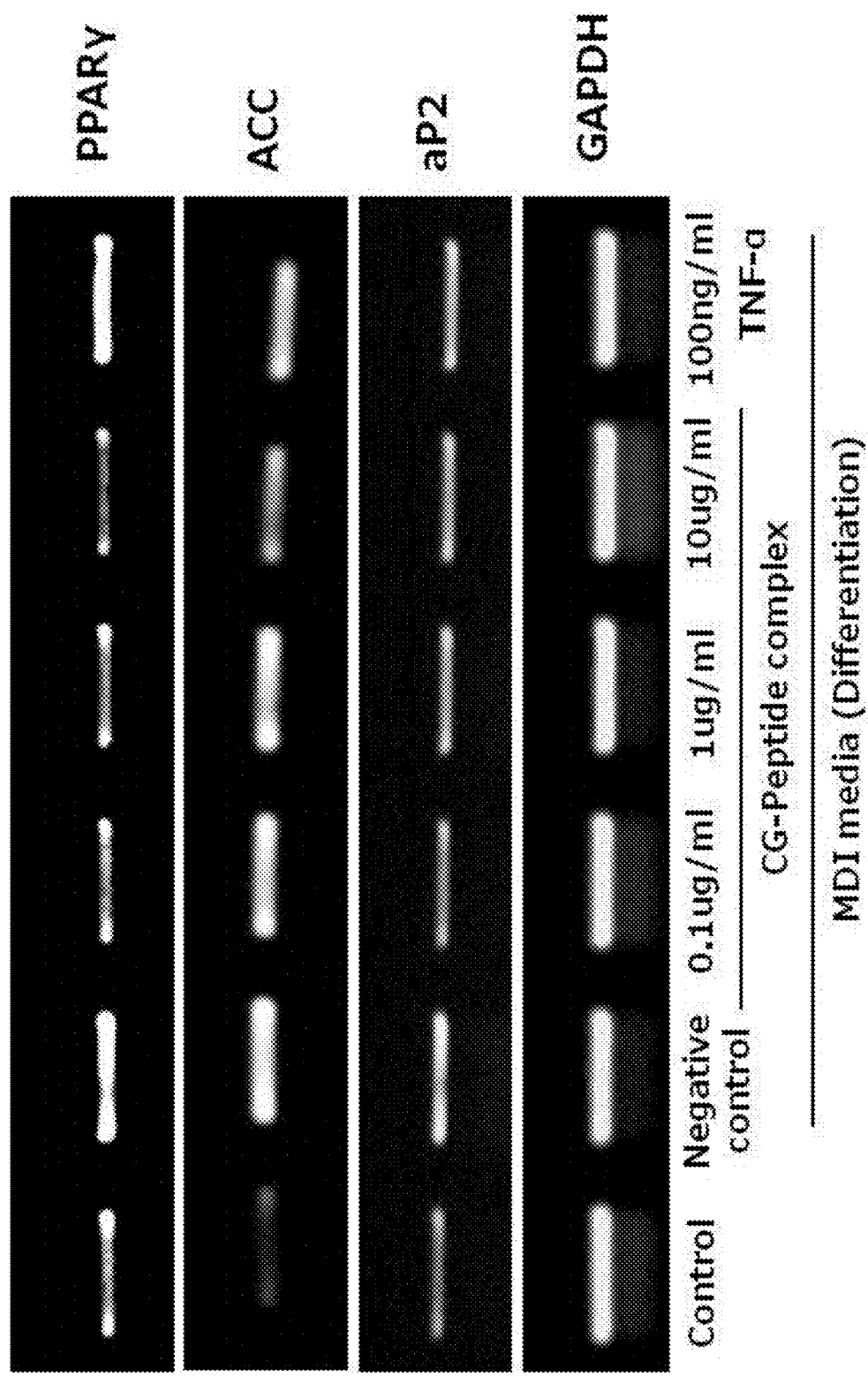
FIG. 4 shows the measured results of the expression levels of the genes PPARγ, ACC, and aP2, which play an important role in adipogenesis, after treatment with various concentrations of the peptide complexes according to an embodiment of the present invention.

As shown in FIG. 4, it was observed that when the mouse osteoblast cell line 3T3-L1 were incubated for three days after treatment with the peptide complexes at a concentration of 0.1 µg/ml, 1 µg/ml, and 10 µg/ml, the expression levels of the adipogenic markers PPARγ, ACC, and aP2 were also decreased in both the positive control group treated with 100 ng/ml of TNFα and the peptide complex-treated group.

1-3. Observation of Expression Levels of Adipogenesis- and Lipolysis-Inducing Proteins Using Pre-Adipocyte 3T3-L1 cells (pre-adipocytes) were seeded at a density of 3×10⁵ cells/well into 6-well plates. After incubating for 24 hours, the cells were incubated for 14 days in a 37° C. incubator after treatment with various concentrations (0.1, 1, and 10 µg/ml) of the peptide complexes. Cell lysates obtained by treatment with a cell lysis buffer were used for protein quantitation, and then Western blotting was performed using an anti-PPARγ antibody (Santa Cruz Biotechnology, USA), which is an antibody against an adipogenic marker, and an anti-pHSL antibody (Santa Cruz Biotechnology, USA), which is an antibody against an lipolytic factor.

Figure 5A:
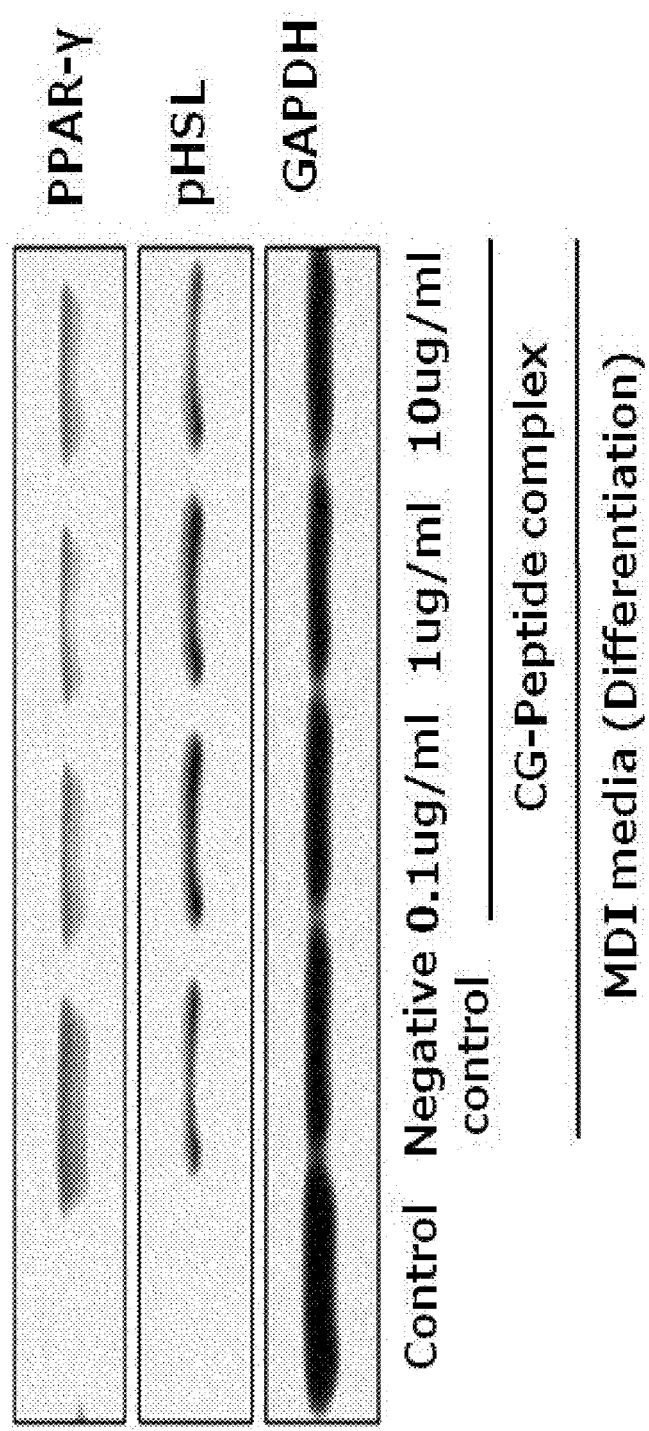
FIG. 5a shows the measured results of the expression levels of the PPARγ protein, which plays an important role in adipogenesis, and the phospho-HSL protein, which plays an important role in lipolysis, after treatment with various concentrations of the peptide complexes according to the present invention.
Figure 5B:
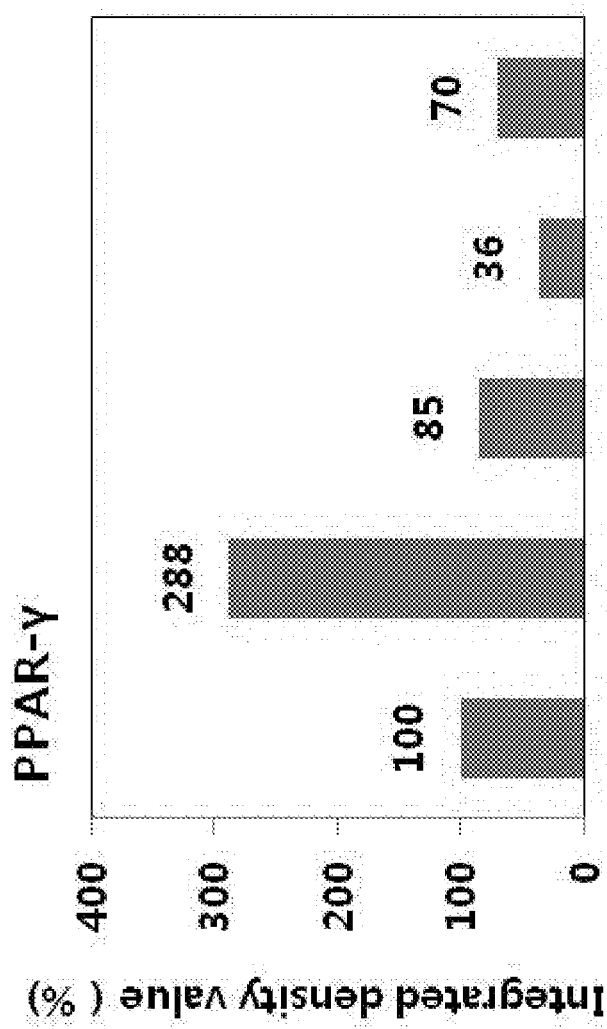
FIG. 5b is a graph showing the measured results of the expression levels of the PPARγ protein, which plays an important role in adipogenesis, after treatment with various concentrations of the peptide complexes according to the present invention.
Figure 5C:
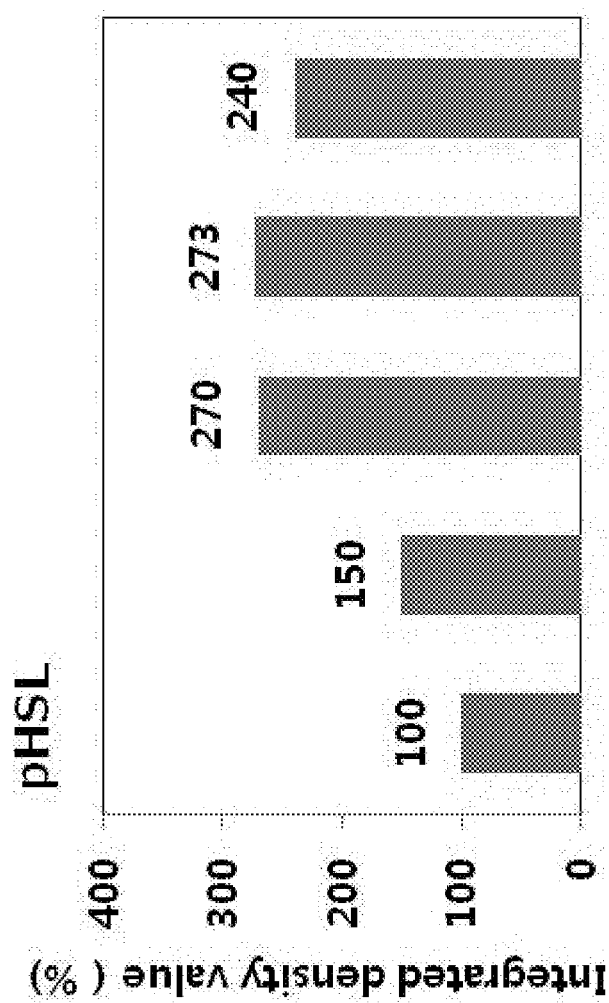
FIG. 5c is a graph showing the measured results of the expression levels of the phospho-HSL protein, which plays an important role in lipolysis, after treatment with various concentrations of the peptide complexes according to the present invention.

As shown in FIG. 5, it was observed that the expression levels of the adipogenic marker PPARγ protein after treatment with various concentration of the peptide complexes were all decreased in a dose-dependent manner, and the expression levels of the lipolytic factor pHSL protein were all decreased in the the peptide complex-treated group.

Example 2: Assay for Lipolytic Activity 2-1. Increased Expression Levels of Genes Involved in Lipolysis 3T3-L1 cells (pre-adipocytes) were seeded at a density of 3×10⁵ cells/well into 6-well plates. After incubating for 24 hours, the cells were incubated for 14 days in a 37° C. incubator after treatment with various concentrations (0.1, 1, and 10 µg/ml) of the peptides (positive control group: 100 ng/ml of TNFα(SIGMA)). Thereafter, the cells were harvested and treated with an RNA extraction solution (Easy Blue, Intron) to prepare RNA from which cDNA was then synthesized using an RT premix (Intron). PCR was performed using primers for the markers (AMPK-al, CGI58), and a PCR premix (Intron). Next, the PCR products were each loaded in an amount of 5 µl into a 1% agarose gel and electrophoresis was performed, and then bands were identified in a Gel-Doc. The results are shown in FIG. 6.

Target-specific primer sequences for PCR of adipogenic markers are as follows:

| SEQ ID NO. | Primer | Sequence (5'-3') | Annealing Temperature (° C.) |
|---|---|---|---|
| 14 | AMPK-1_F | TGACCGGACATAAAGTGGCTGTGA | 60 |
| 15 | AMPK-1_R | TGATGATGTGAGGGTGCCTGAACA | 60 |
| 16 | CGI58_F | TGTGCAGGACTCTTACTTGGCAGT | 60 |
| 17 | CGI58_R | GTTTCTTTGGGCAGACCGGTTTCT | 60 |

Figure 6A:
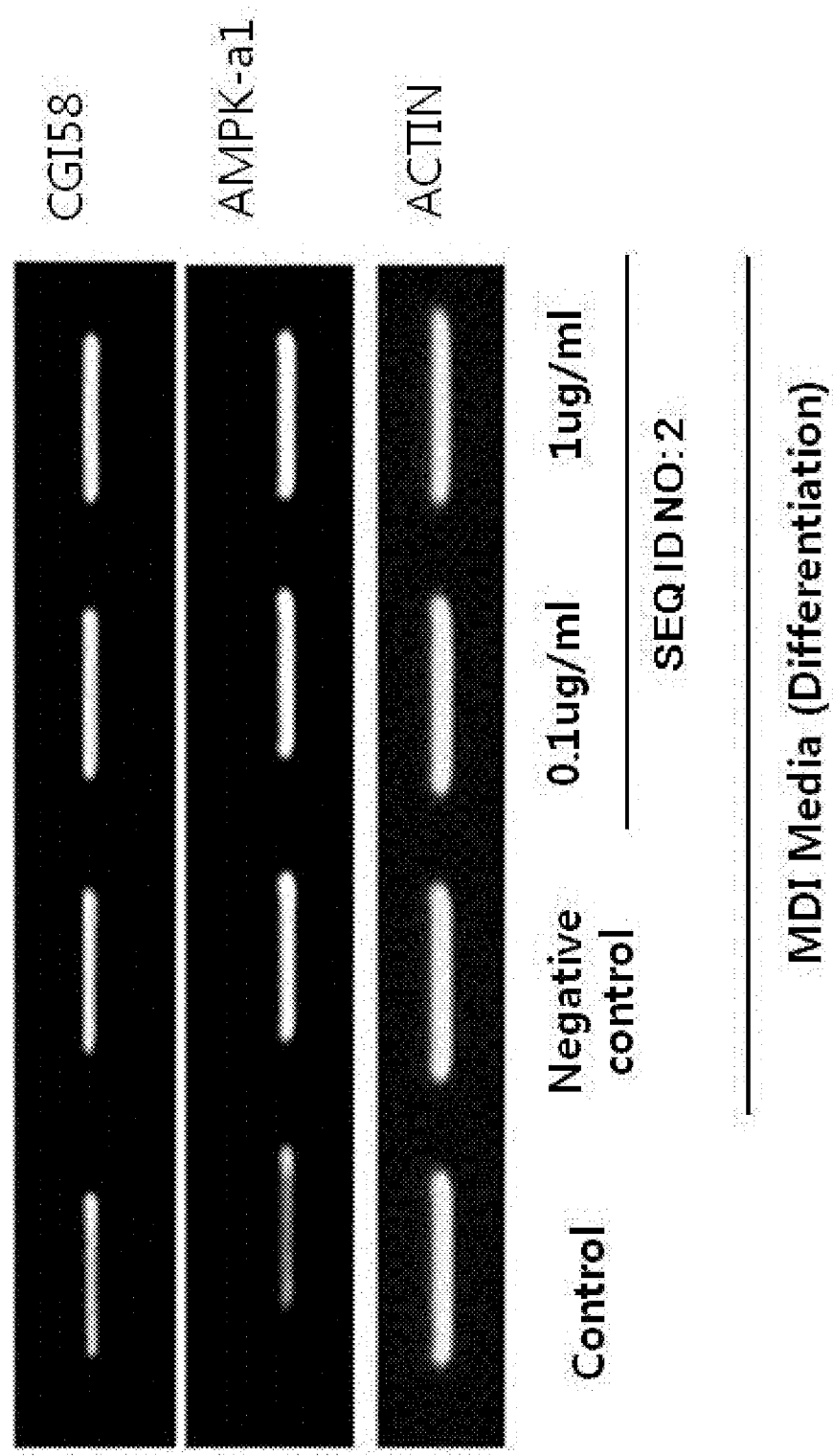
FIG. 6a shows the measured results of the expression levels of the genes AMPK-α1 and CGI58, which are involved in the decomposition of accumulated fats, after treatment with the peptide consisting of the amino acid sequence of SEQ ID NO: 2 according to an embodiment of the present invention.
Figure 6B:
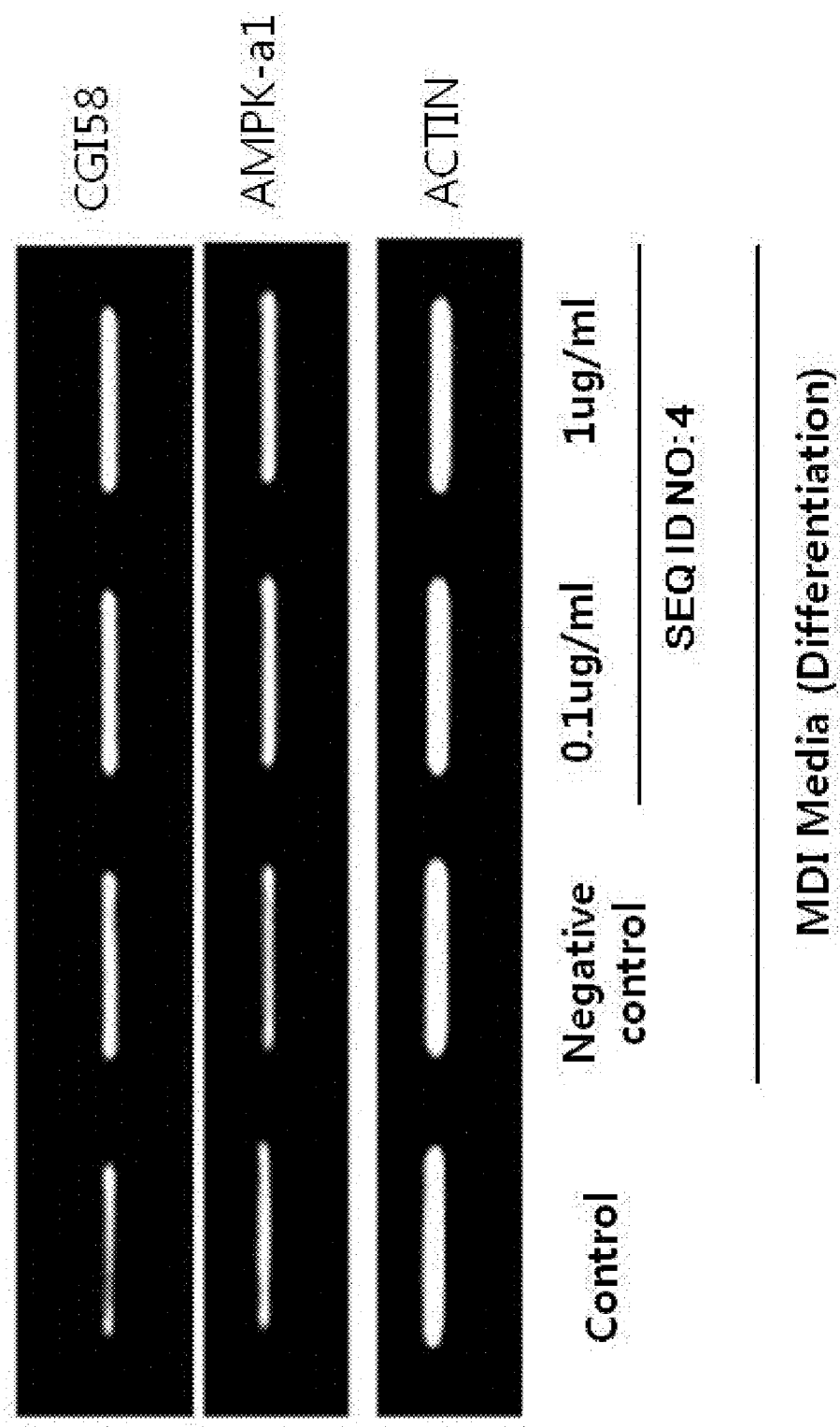
FIG. 6b shows the measured results of the expression levels of the genes AMPK-α1 and CGI58, which are involved in the decomposition of accumulated fats, after treatment with the peptide consisting of the amino acid sequence of SEQ ID NO: 4 according to an embodiment of the present invention.

As shown in FIGS. 6a and 6b, it was observed that in the pre-adipocytes (3T3-L1) which were incubated after treatment with the peptides, the expression levels of the adipogenic marker the lipolytic factors AMPK-α1 and CGI-58 were increased in all the peptides-treated group.

Figure 6C:
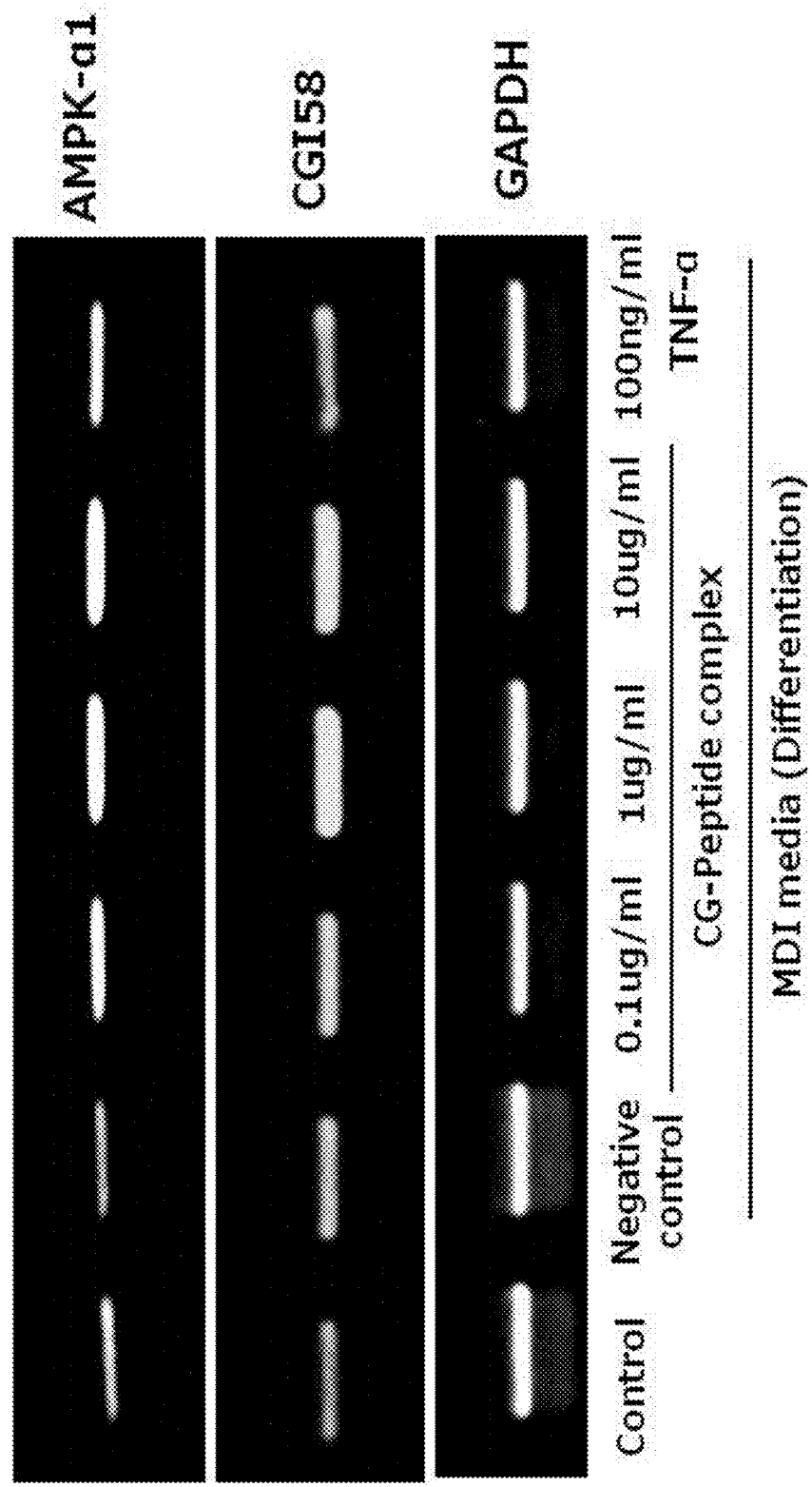
FIG. 6c shows the measured results of the expression levels of the genes AMPK-α1 and CGI58, which are involved in the decomposition of accumulated fats, after treatment with the peptide complexes according to an embodiment of the present invention.

As shown in FIG. 6c, it was observed that, the expression levels of AMPK-α1 and CGI-58 after treatment with the peptide complexes were increased in a dose-dependent manner, and the expression levels of the lipolytic factors were higher compared to the positive control group treated with 100 ng/ml of TNFα.

2-2. Observation of Expression Levels of Lipolysis-Inducing Proteins Using Pre-Adipocyte 3T3-L1 cells (pre-adipocytes) were seeded at a density of 3×10$^5$ cells/well into 6-well plates. After incubating for 24 hours, the cells were incubated for 14 days in a 37° C. incubator after treatment with various concentrations (0.1, 1, and 10 μg/ml) of the peptide complexes (positive control group: 100 ng/ml of TNFα(SIGMA)). Cell lysates obtained by treatment with a cell lysis buffer were used for protein quantitation, and then Western blotting was performed using an anti-ATGL antibody (Santa Cruz Biotechnology, USA), which is an antibody against an lipolytic factor.

Figure 7A:
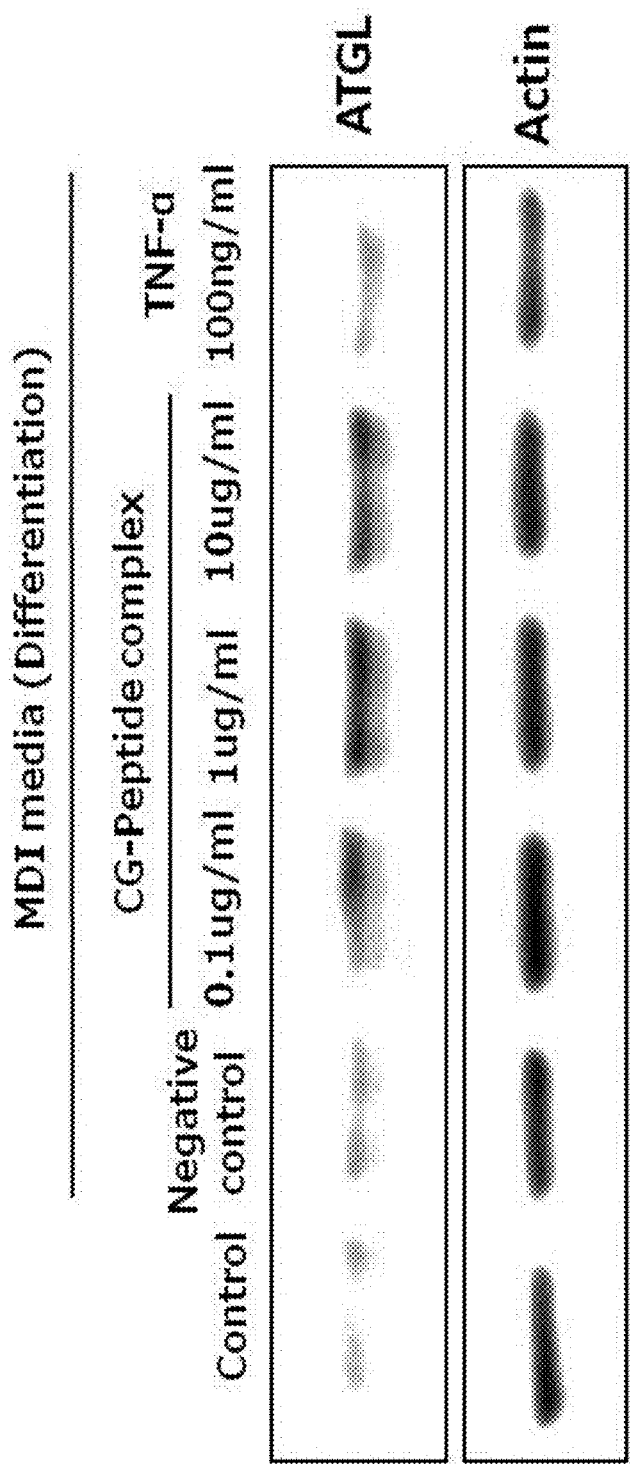
FIG. 7a shows is a photograph showing the measured results of the expression levels of the ATGL protein, which is involved in the decomposition of accumulated fats, after treatment with various concentrations of the peptide complexes according to the present invention.
Figure 7B:
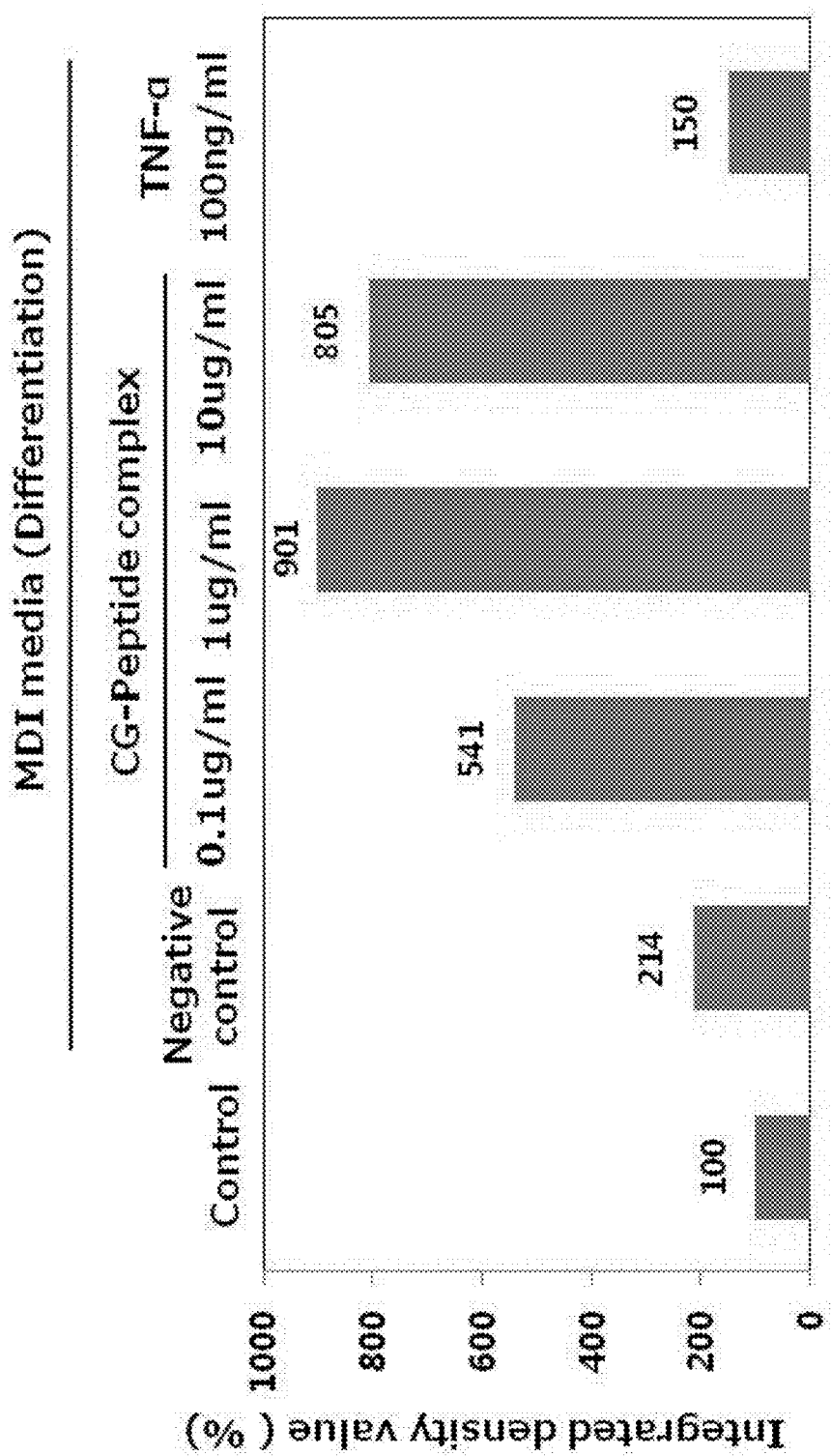
FIG. 7b shows is a graph showing the measured results of the expression levels of the ATGL protein, which is involved in the decomposition of accumulated fats, after treatment with various concentrations of the peptide complexes according to the present invention.

As shown in FIG. 7, it was confirmed that the expression levels of the lipolytic factor ATGL were increased by treatment with the peptide complexes.

2-3. Fluorescence Microscopic Observation of Expression Levels of Lipolysis-Inducing Proteins Using Pre-Adipocyte 3T3-L1 cells (pre-adipocytes) were seeded at a density of 3×10$^5$ cells/well into 6-well plates. After incubating for 24 hours, the cells were incubated for 14 days in a 37° C. incubator after treatment with each peptide or peptide complex (1 μg/ml) (positive control group: 100 ng/ml of TNFα (SIGMA)). Thereafter, the cells were fixed with 70% ethanol, and then subjected to immunostaining with an anti-phospho-HSL antibody (Santa Cruz Biotechnology, USA) to observe the cellular expression levels of phospho-HSL, a lipolytic factor.

Figure 8A:
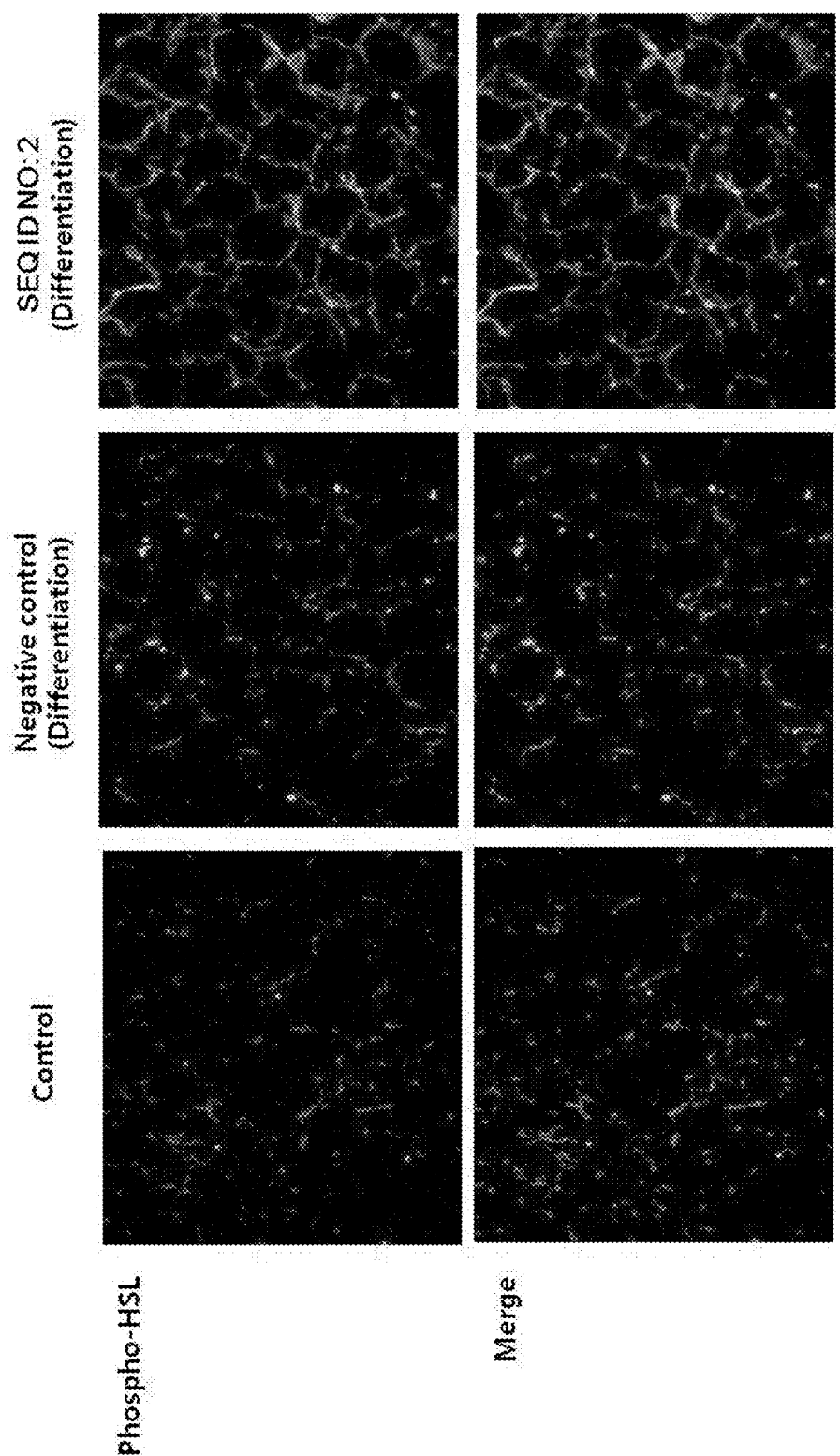
FIG. 8a shows the results of the expression levels of the Phospho-HSL protein, which is involved in the decomposition of accumulated fats, after treatment with the peptide consisting of the amino acid sequence of SEQ ID NO: 2 according to an embodiment of the present invention, as analyzed by immunostaining.
Figure 8B:
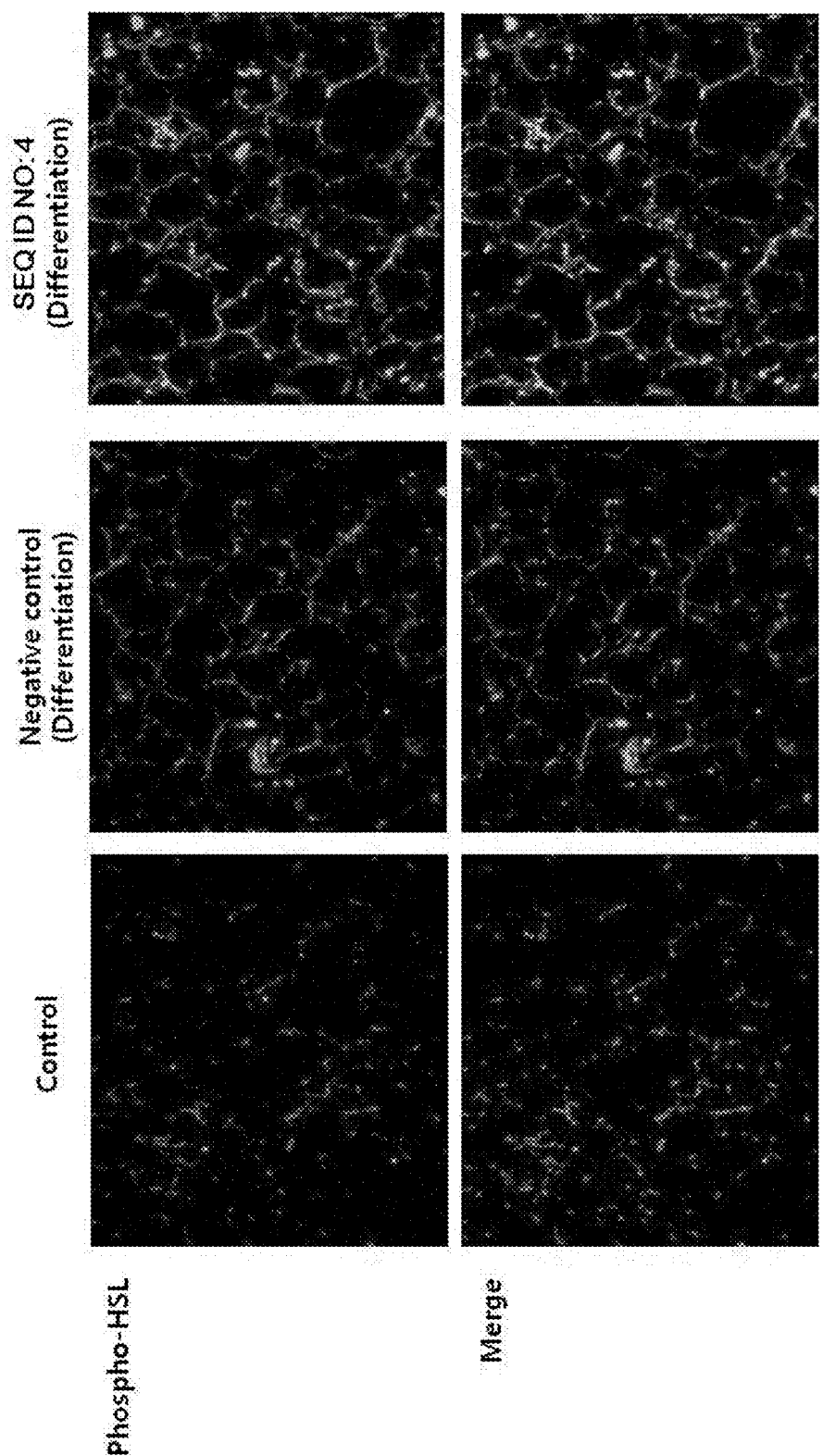
FIG. 8b shows the results of the expression levels of the Phospho-HSL protein, which is involved in the decomposition of accumulated fats, after treatment with the peptide consisting of the amino acid sequence of SEQ ID NO: 4 according to an embodiment of the present invention, as analyzed by immunostaining.
Figure 8C:
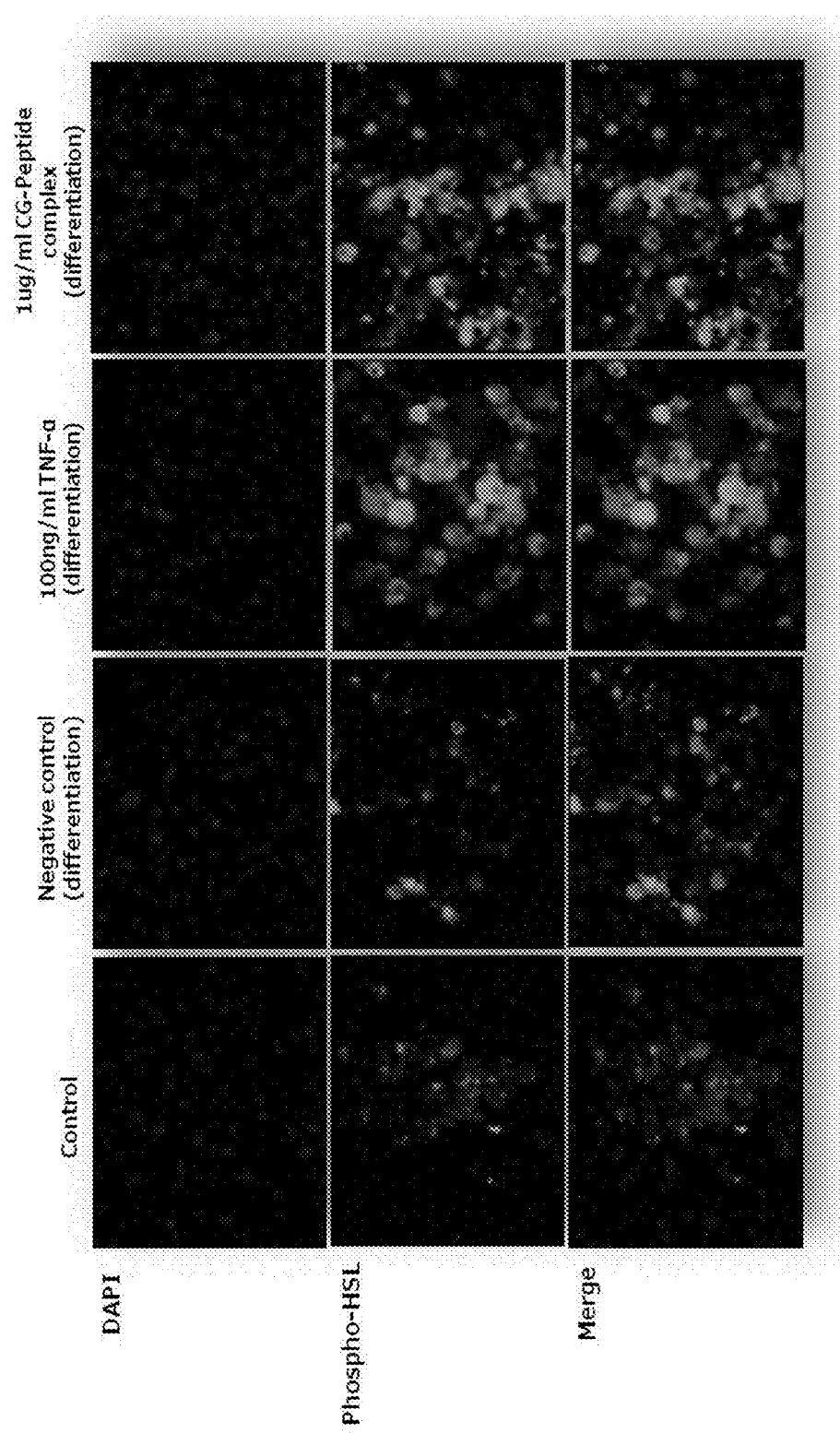
FIG. 8c shows the results of the expression levels of the Phospho-HSL protein, which is involved in the decomposition of accumulated fats, after treatment with the peptide complexes according to an embodiment of the present invention, as analyzed by immunostaining.

As shown in FIGS. 8a to 8c, it was confirmed that the expression levels of the lipolytic factor phospho-HSL after treatment with each peptide (see FIGS. 8a and 8b) and peptide complex (see FIG. 8c) were increased.

2-4. Quantitation of Lipolysis Product Glycerol

Adipose tissues were taken from the abdomens of obesity-induced mice and plated at an amount of 100 mg/well into 24-well culture plates, and then incubated in a culture medium (1 ml Krebs-Ringer buffer containing 25 mM HEPES, 5.5 mM glucose, and 2% (w/v) bovine serum albumin). At the time of incubation, the tissues were incubated for 48 hours after treatment with 0.1 μg/ml, 1 μg/ml, and 10 μg/ml of the peptide complexes, and 100 ng/ml of TNFα as a positive control. Glycerol produced during lipolysis was quantitatively measured.

Figure 9:
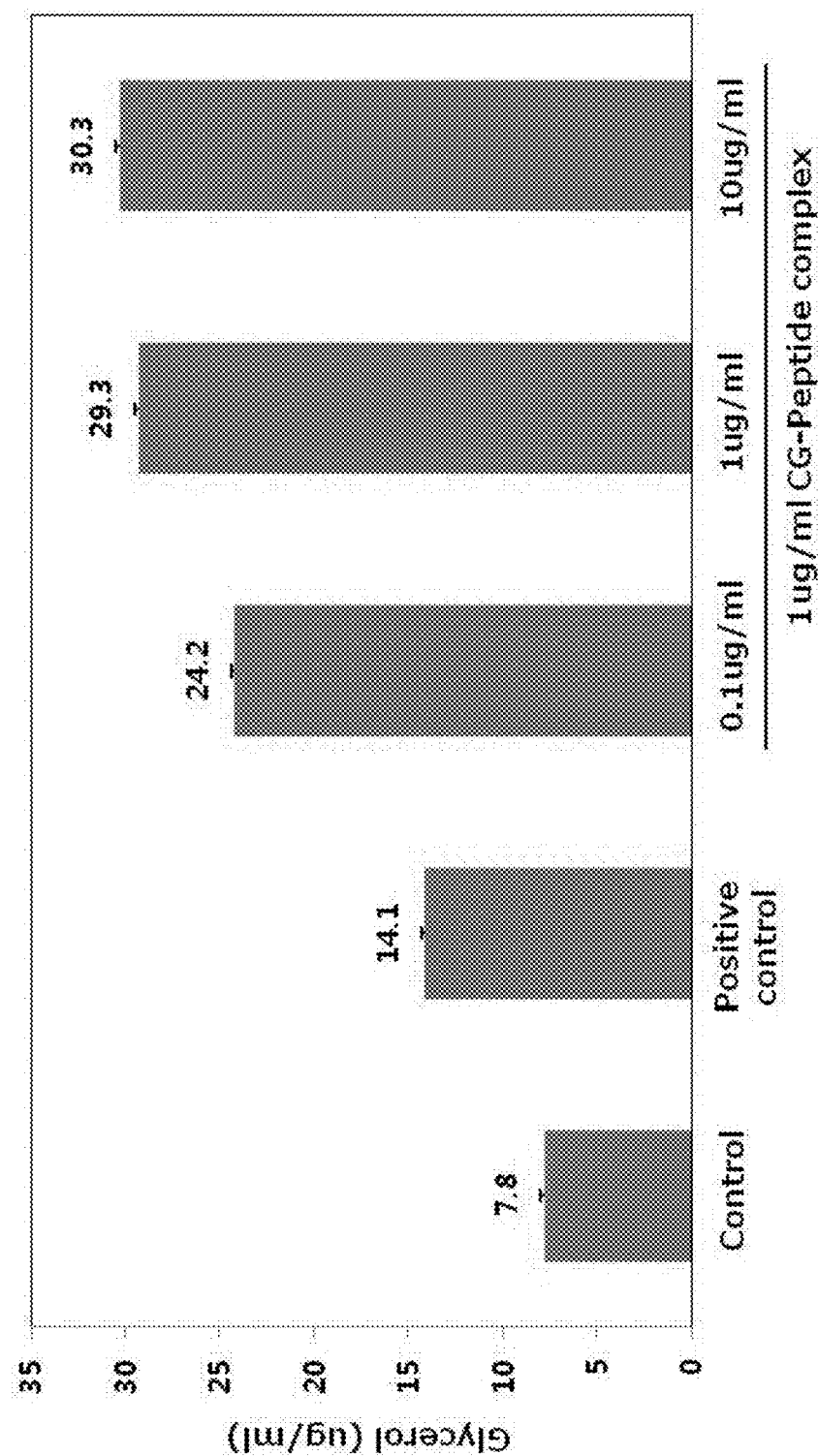
FIG. 9 shows the measured results of the produced glycerol levels, after treatment with various concentrations of the peptide complexes according to the present invention.

As shown in FIG. 9, it was confirmed that the amount of glycerol resulting from lipolysis after treatment with various concentration of peptide complexes was increased in a dose-dependent manner. It was confirmed that the amount of glycerol was also greater than that resulting from the positive control group treated with TNFα.

2-5. Lipolytic Effect on Adipose Tissues Isolated From Obese Mouse

Adipose tissues are classified into white fat and brown fat depending on the color and are classified into subcutaneous fat, abdominal fat, mesentery fat (visceral fat), and epididymal fat depending on the site. After dissection, each fat was extracted to isolate white fats. The white fats were placed at an amount of 100 mg/well into 24-well culture plates, and then incubated for 72 hours in a culture medium (1 ml Krebs-Ringer buffer containing 25 mM HEPES, 5.5 mM glucose, and 2% (w/v) bovine serum albumin) after treatment with various concentrations of the peptide complexes. The fats were sectioned into slices and were dyed with hematoxylin and eosin. Sizes of adipocytes were compared under a microscope (TS100, Nikon) with 200× magnification.

Figure 10A:
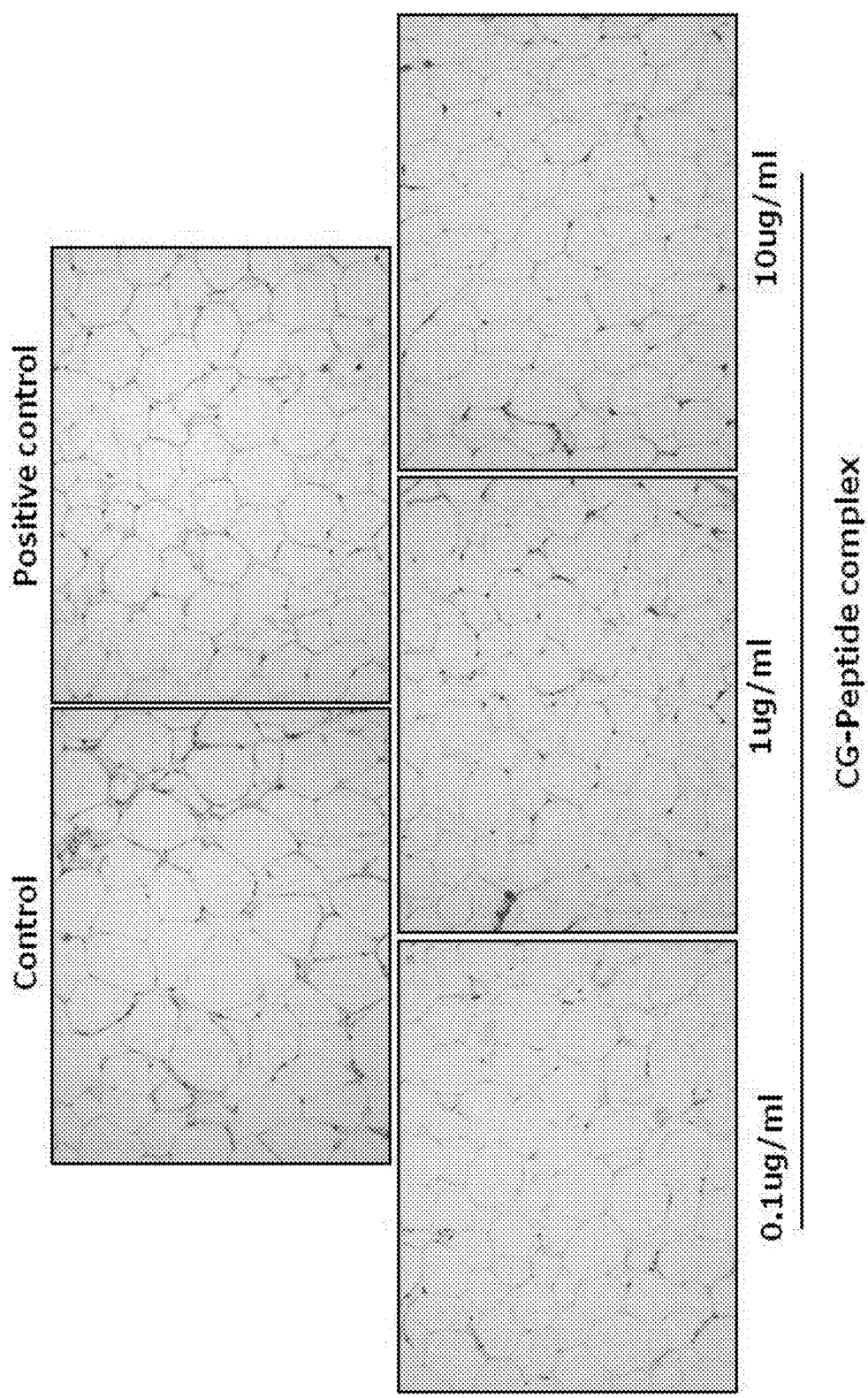
FIG. 10a shows the measured results of the decomposed adipose tissues, after treatment with various concentrations of the peptide complexes according to the present invention in an experimental model of obese mice.

As shown in FIG. 10a, it was confirmed that the fats after treatment with various concentrations of the peptide complexes decreased in size compared to the control group.

Figure 10B:
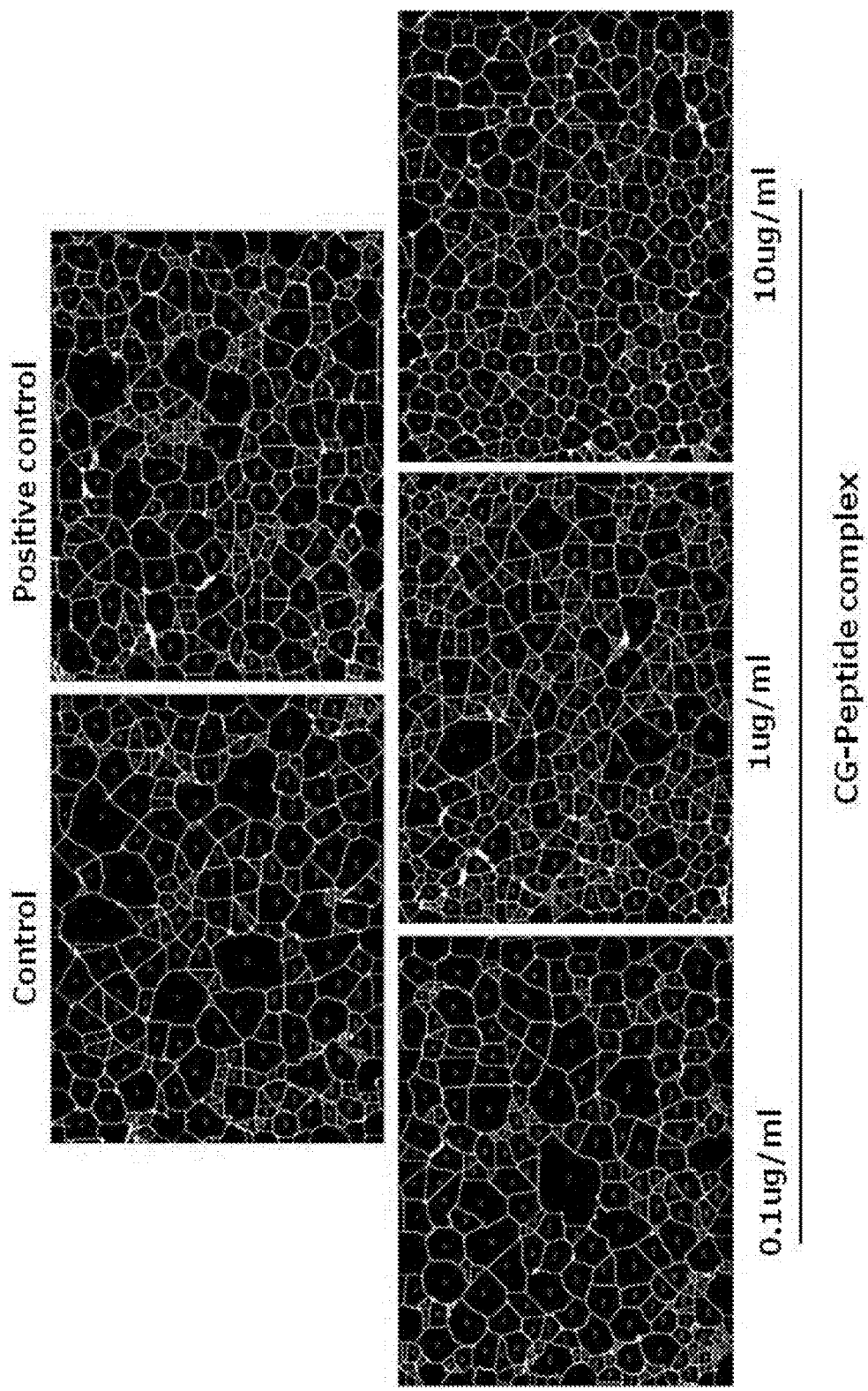
FIG. 10b shows the measured results of sizes and numbers of the decomposed adipose tissues, after treatment with the peptide complexes according to the present invention in an experimental model of obese mice.

As shown in FIG. 10b, it was observed that as a result of measuring the size of the adipocytes using the program after dying, the size of the cells in adipose tissues having distinct cell membrane compartments were decreased in the peptide complex-treated group.

2-6. Observation of Lipolytic Factor in Adipose Tissues

Adipose tissues were taken from the abdomens of obesity-induced mice and plated at an amount of 100 mg/well into 24-well culture plates, and then incubated in a culture medium (1 ml Krebs-Ringer buffer containing 25 mM HEPES, 5.5 mM glucose, and 2% (w/v) bovine serum albumin). At the time of incubation, the tissues were incubated for 48 hours after treatment with the peptide complexes, and 100 ng/ml of TNFα as a positive control. The expression of the labeled lipolytic factor phospho-HSL (green fluorescent substance) was confirmed.

Figure 11:
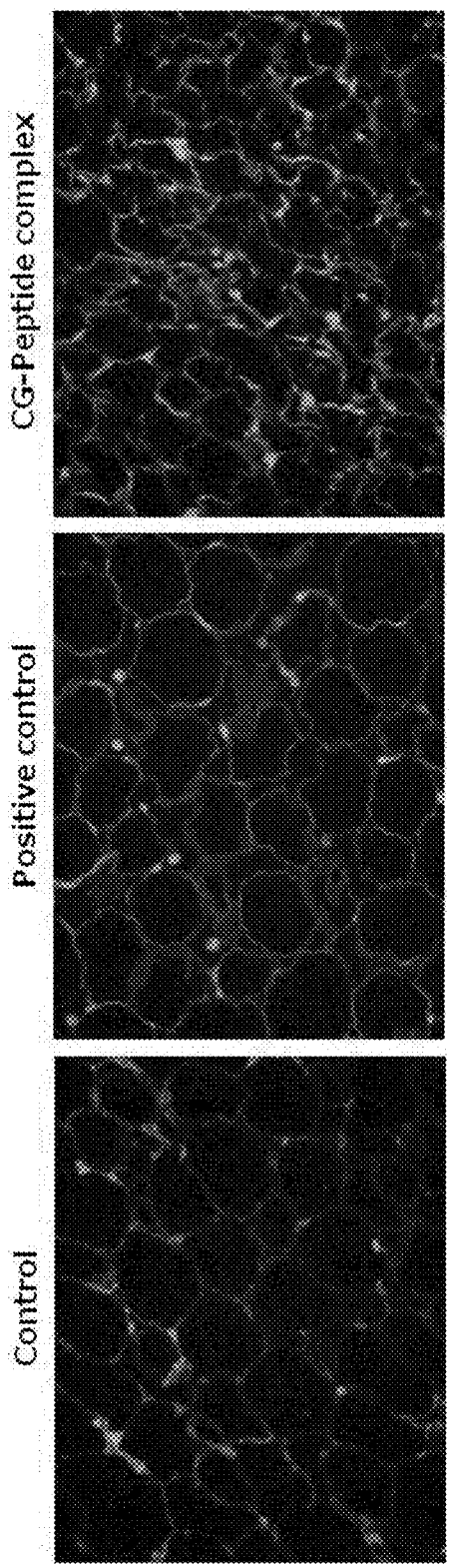
FIG. 11 shows the measured results of the expression levels of the Phospho-HSL protein, which is involved in the decomposition of accumulated fats, after treatment with the peptide complexes according to the present invention, as analyzed by immunostaining.

As shown in FIG. 11, it was confirmed that the expression levels of the lipolytic factor phospho-HSL in adipose tissues were increased after treatment with the peptide complex.

Example 3: Adipogenesis-Suppressive and Lipolysis-Promotive Effect in Experimental Animal Obesity-induced Models DIO (diets induced obesity), which had become obese by feeding high-fat diets to normal C57BL/6 mouse, were used for the anti-obesity experiment in which 5 μg/ml of TNFα was used as a positive control drug. For a control, a general diet, not a high-fat diet, was fed. In this experiment, a high-fat diet was fed for 12 weeks, while the peptide complexes or the positive control drug were applied. During the experiment, the weight loss was confirmed.

TNFα and the anti-obesity active compounds were intraperitoneally injected at 3:00 to 4:00 pm every week for 12 weeks. Body weights and dietary amounts were measured just before the first drug injection, and then measured at weekly intervals.

Blood samples were collected from the tail vein after the end of the drug injection experiment, and then blood sugar levels were measured using Accu-Check Active (Roche) and cholesterol levels were analyzed using Cholesterol calculation Kit (BioVision).

Adipose tissues are classified into white fat and brown fat depending on the color and are classified into subcutaneous fat, abdominal fat, mesentery fat (visceral fat), and epididymal fat depending on the site. After dissection, each fat was extracted. For histological examination, the fats were fixed with 10% neutral buffered formalin, embedded in paraffin blocks, cut into 5 μM-thick sections, and dyed with hematoxylin and eosin.

To analyze the degree of phosphorylation of the lipolytic factor HSL, fluorescent staining was carried out using an anti-pHSL antibody. The tissue samples were prepared, mounted on glycerine jell mounting media, and covered with a cover glass. The tissues were taken with a digital camera built into a microscope (Nikon, TS100) and images were observed under the microscope.

Figure 12:
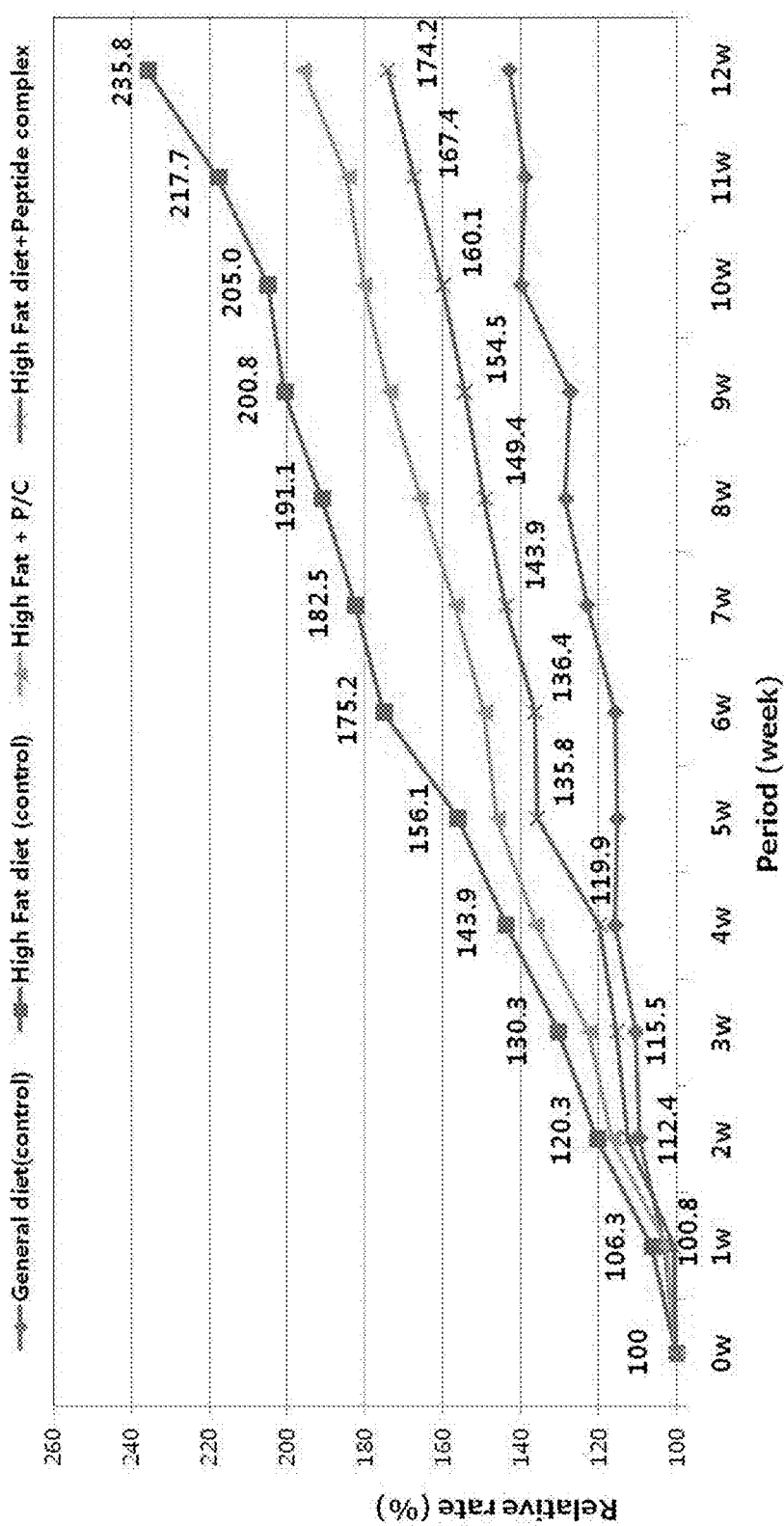
FIG. 12 shows the measured results of changes in (a) body weight and (b) feed intake of obese mice, after treatment with the peptide complexes according to the present invention.

It was confirmed that there was the body gain of mice from 20.9 g to 28.74 g when fed with a general diet and from 20.99 g to 49.5 g when fed with a high-fat diet, for 12 weeks from the beginning of the experiment to the end of the experiment. However, it was confirmed that there was the weight gain of both the high-fat diet-fed and peptide complex-treated group from 21.1 g to 36.76 g for 12 weeks from the beginning of the experiment to the end of the experiment, indicating a significant decrease of weight gain (174.2%) compared to the high-fat diet-fed control group (235.8%) (see Tables 4 and 5 and FIG. 12). Tables 4 and 5 show the measured results of the body weight in gram (g) and percentage (%) after treatment with peptide complexes in obese mouse models.

TABLE 4

| Week | General Diet (control) | High-Fat Diet (control) | H.F + P/C | H.F + P. Complex |
|---|---|---|---|---|
| 0 | 20.09 | 20.99 | 22.41 | 21.10 |
| 1 | 20.75 | 22.32 | 23.00 | 21.26 |
| 2 | 21.99 | 25.25 | 26.12 | 23.72 |
| 3 | 18.23 | 27.35 | 27.45 | 24.36 |
| 4 | 23.26 | 30.20 | 30.51 | 25.29 |
| 5 | 23.16 | 32.76 | 32.76 | 28.65 |
| 6 | 23.28 | 36.78 | 33.49 | 28.79 |
| 7 | 24.71 | 38.31 | 35.14 | 30.37 |
| 8 | 25.84 | 40.12 | 37.15 | 31.53 |
| 9 | 25.59 | 42.14 | 38.97 | 32.59 |
| 10 | 28.13 | 43.02 | 40.39 | 33.78 |
| 11 | 27.90 | 45.70 | 41.35 | 35.33 |
| 12 | 28.74 | 49.50 | 43.91 | 36.76 |

TABLE 5

| Week | General Diet (control) | High-Fat Diet (control) | H.F + P/C | H.F + P. Complex |
|---|---|---|---|---|
| 0 | 100 | 100 | 100 | 100 |
| 1 | 103.3 | 106.3 | 102.6 | 100.8 |
| 2 | 109.5 | 120.3 | 116.6 | 112.4 |
| 3 | 90.7 | 130.3 | 122.5 | 115.5 |
| 4 | 115.8 | 143.9 | 136.1 | 119.9 |
| 5 | 115.3 | 156.1 | 146.2 | 135.8 |
| 6 | 115.9 | 175.2 | 149.4 | 136.4 |
| 7 | 123.0 | 182.5 | 156.8 | 143.9 |
| 8 | 128.6 | 191.1 | 165.8 | 149.4 |
| 9 | 127.4 | 200.8 | 173.9 | 154.5 |
| 10 | 140.0 | 205.0 | 180.2 | 160.1 |
| 11 | 138.9 | 217.7 | 184.5 | 167.4 |
| 12 | 143.1 | 235.8 | 195.9 | 174.2 |

Figure 13:
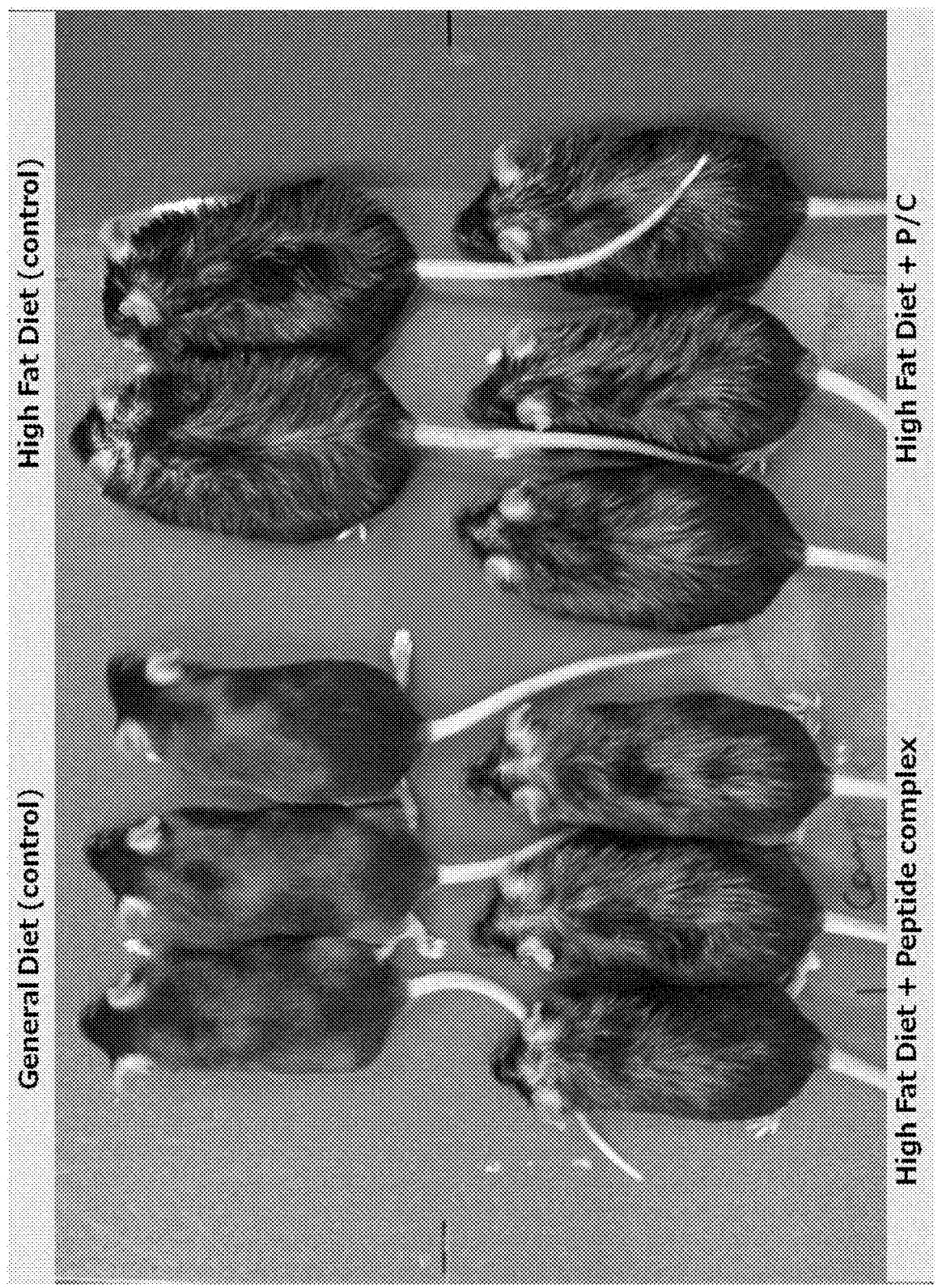
FIG. 13 shows the measured results of images of obese mice, after treatment with the peptide complexes according to the present invention.

As shown in FIG. 13, it was observed that after completion of the 12-week experiment, the body sizes of the peptide complex-treated group were maintained similar to those of the normal mice (general diet) compared to those of the high-fat diet-fed group, as analyzed on the photographs.

TABLE 6

| | Total Volume (mm³) | Total Fat (mm³) | Visceral Fat (mm³) | Subcutaneous Fat (mm³) |
|---|---|---|---|---|
| Control (General Diet) | 4958.25 | 702.72 | 380.09 | 322.63 |
| HFD (2 weeks) | 6530.09 | 2084.98 | 1411.14 | 673.84 |
| HFD (10 weeks) | 12464.91 | 8014.03 | 5821.27 | 2192.76 |
| HDF (10 weeks) + complex (8 weeks) | 6012.12 | 1391.75 | 871.15 | 520.60 |
| HDF (10 weeks) + P.C (8 weeks) | 8240.67 | 4165.80 | 2833.72 | 1332.08 |

Figure 14:
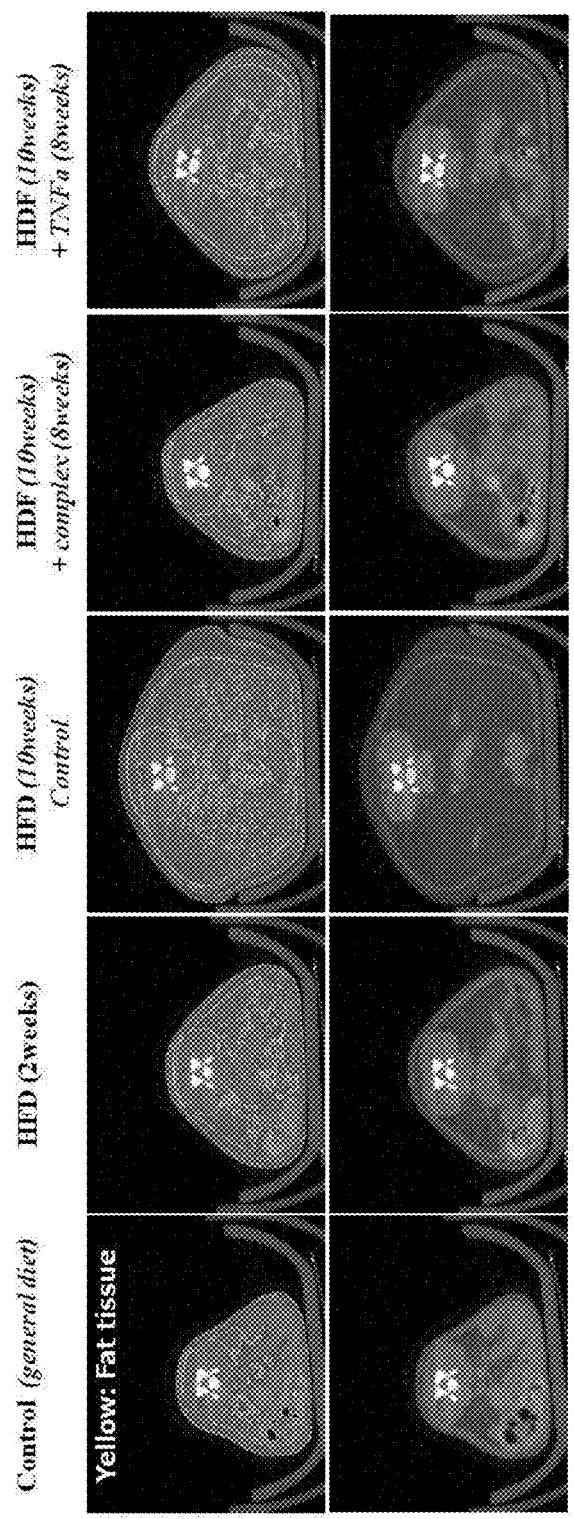
FIG. 14 shows the measured results of fat distribution, after treatment with the peptide complexes according to the present invention in obese mouse models induced by feeding a high-fat feed to a C57BL/6 mouse model, which is an experimental animal model, as analyzed by micro-CT imaging.

As shown in FIG. 14 and Table 6, it was confirmed that as a result of examining the fat (yellow) distributed throughout the mouse body by micro-CT imaging after 12 weeks of the experiment, the amount of the fats distributed throughout the body in the mice of the high-fat diet-fed control group was remarkably increased compared to that of the general diet-fed control group, whereas the amount of the fats distributed throughout the body in both the peptide complex-fed and high-fat diets-fed group was remarkably decreased.

Figure 15:
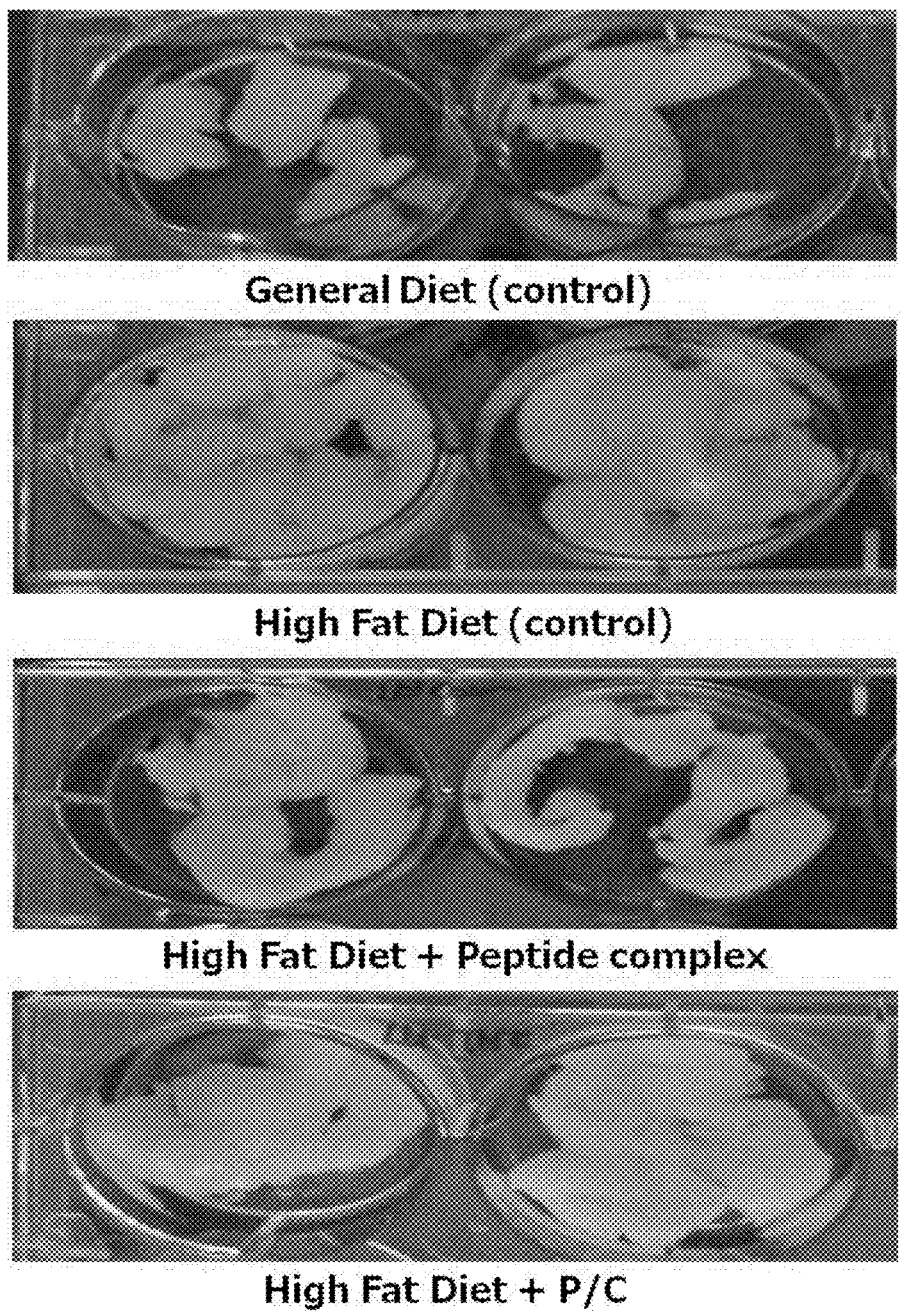
FIG. 15 shows the observed results of obtained adipocyte tissues, after treatment with the peptide complexes according to the present invention in obese mouse models induced by feeding a high-fat feed to a C57BL/6 mouse model, which is an experimental animal model.

As shown in FIG. 15, it was confirmed that as a result of comparing the volumes of adipose tissues after the mice which had completed micro-CT imaging were dissected to extract the adipose tissues distributed throughout the body, the amount of the fats in the mice of the high-fat diet-fed control group was higher than that in the general diet-fed control group, whereas the amount of the fats in both the high-fat diets-fed and peptide complex-fed group was remarkably decreased.

Figure 16A:
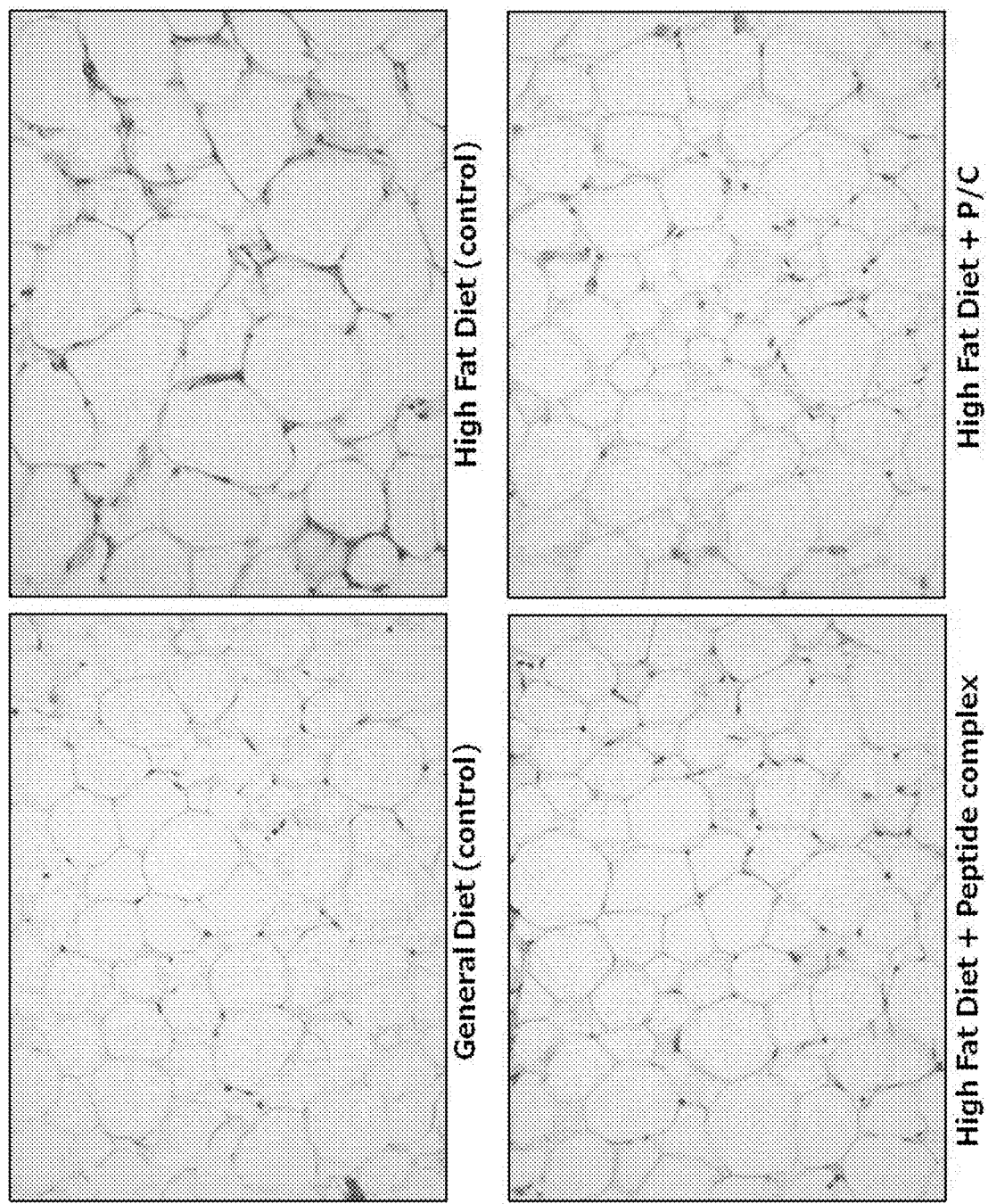
FIG. 16a shows the observed results of morphological images of the adipocytes in obtained adipocyte tissues, after treatment with the peptide complexes according to the present invention in obese mouse models induced by feeding a high-fat feed to a C57BL/6 mouse model, which is an experimental animal model.

As shown in FIG. 16a, it was confirmed that as a result of visualizing fat sizes after fats were isolated and dyed with H&E, the fat size of both the high-fat diets-fed and peptide complex-fed group was smaller than that of the high-fat diet-fed control group.

Figure 16B:
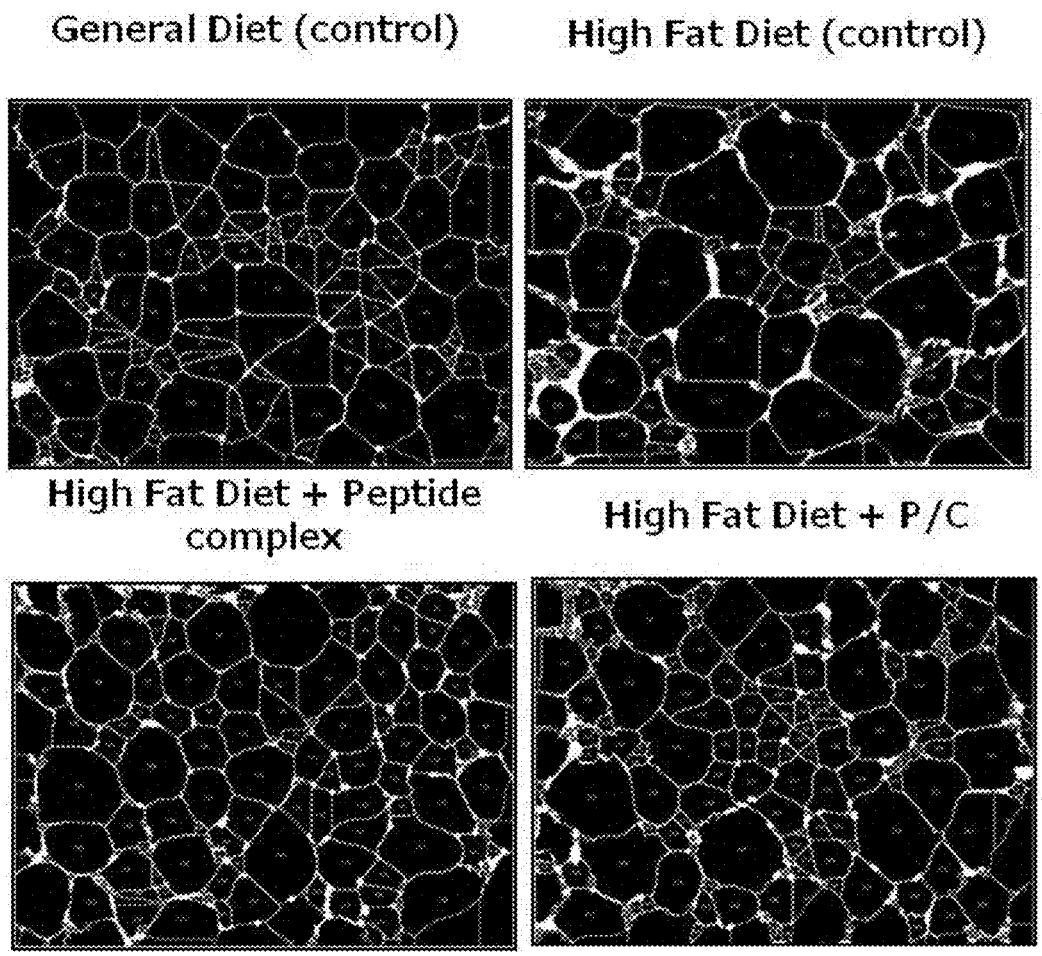
FIG. 16b shows the observed results of sizes of the adipocytes in obtained adipocyte tissues, after treatment with the peptide complexes according to the present invention in obese mouse models induced by feeding a high-fat feed to a C57BL/6 mouse model, which is an experimental animal model.
Figure 16C:
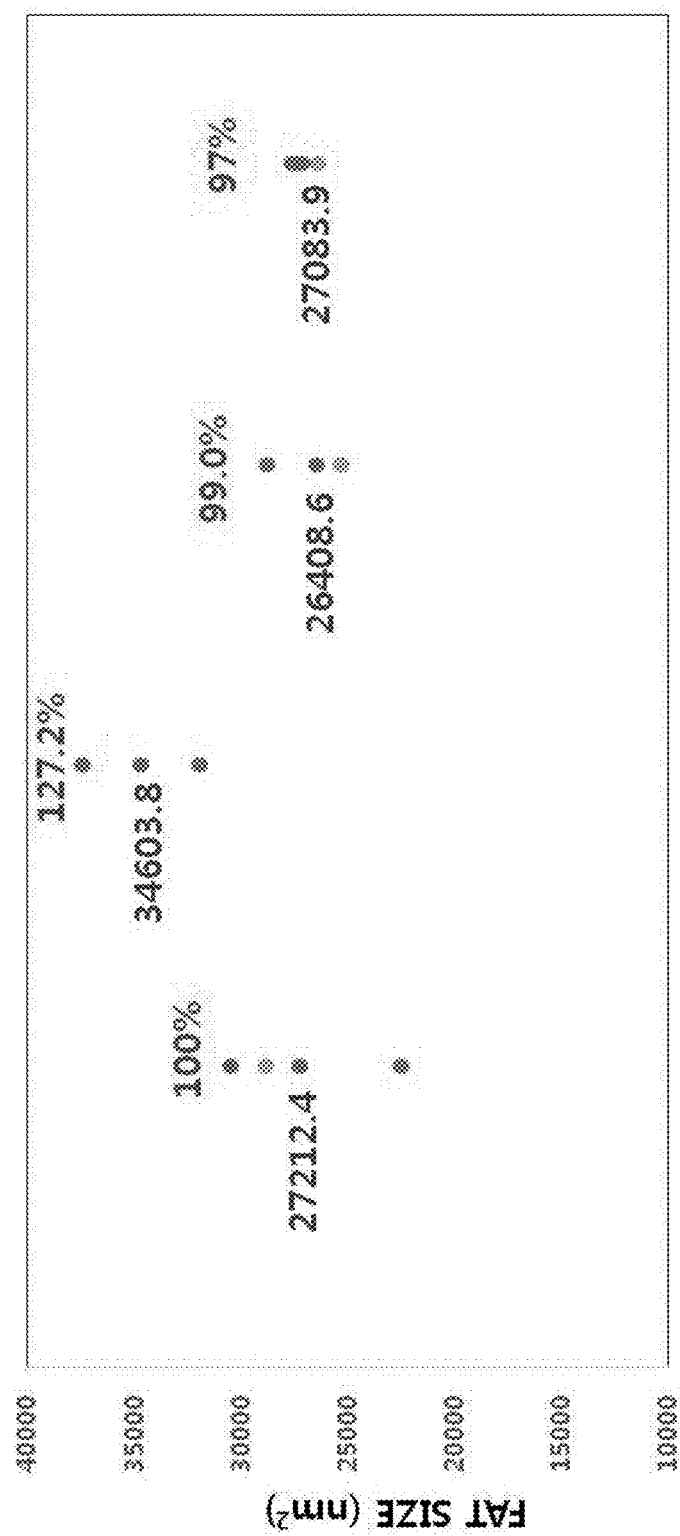
FIG. 16c is a graph showing the observed results of sizes of the adipocytes in obtained adipocyte tissues, after treatment with the peptide complexes according to the present invention in obese mouse models induced by feeding a high-fat feed to a C57BL/6 mouse model, which is an experimental animal model.

As shown in FIGS. 16b and 16c, it was confirmed that as a result of analyzing the size of the fats using the program, when the fat size of the general diet-fed control group was assumed to be 100%, the fat size of the high-fat diet-fed group was increased to 127%, whereas the fat size of the high-fat diets-fed and peptide complex-fed group was decreased to 97%.

Figure 17:
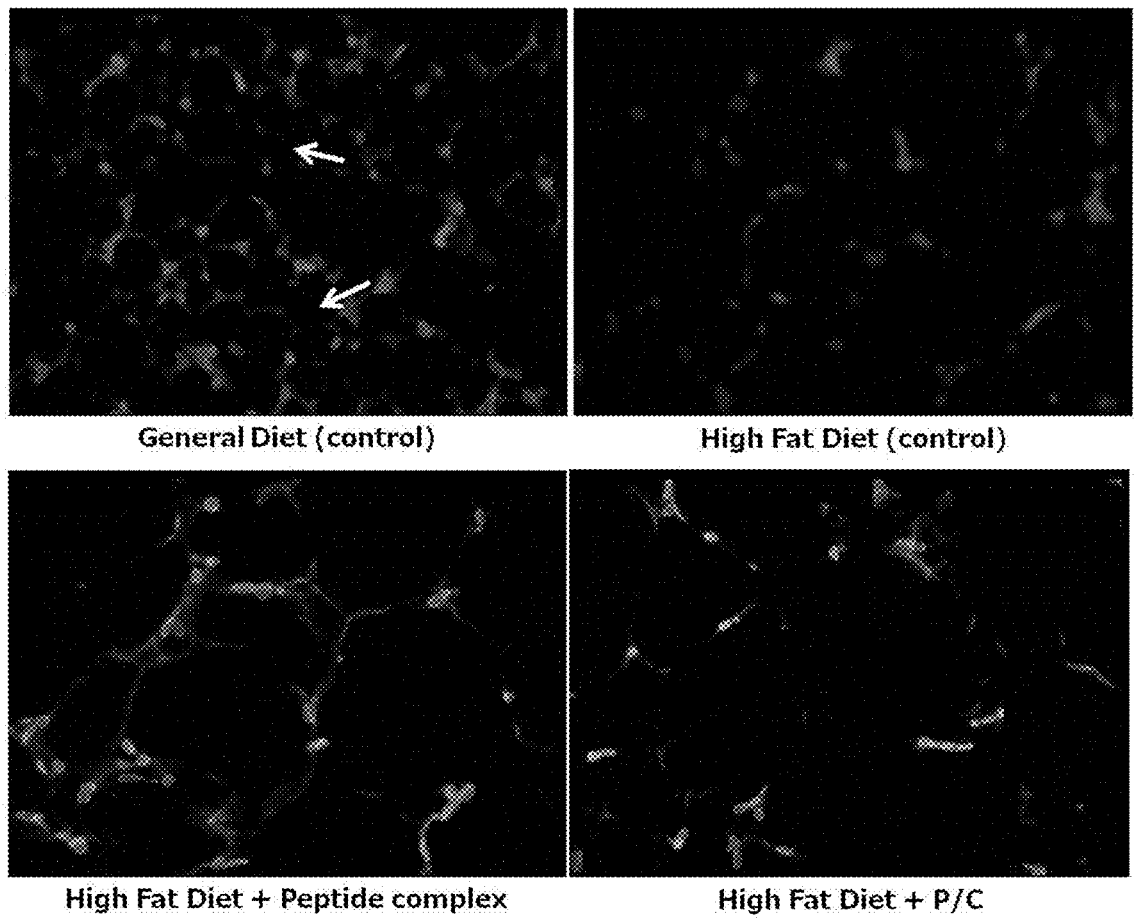
FIG. 17 shows the observed results of the expression levels of the phospho-HSL protein, which is involved in lipolysis, in adipocytes of obtained adipocyte tissues, after treatment with the peptide complexes according to the present invention in obese mouse models induced by feeding a high-fat feed to a C57BL/6 mouse model, which is an experimental animal model.

As shown in FIG. 17, it was confirmed that as a result of measuring the expression levels of the lipolytic factor phospho-HSL expressed in adipose tissues after isolation of fats, the expression levels of phospho-HSL in the high-fat diets-fed and peptide complex-fed group were increased.

Figure 18:
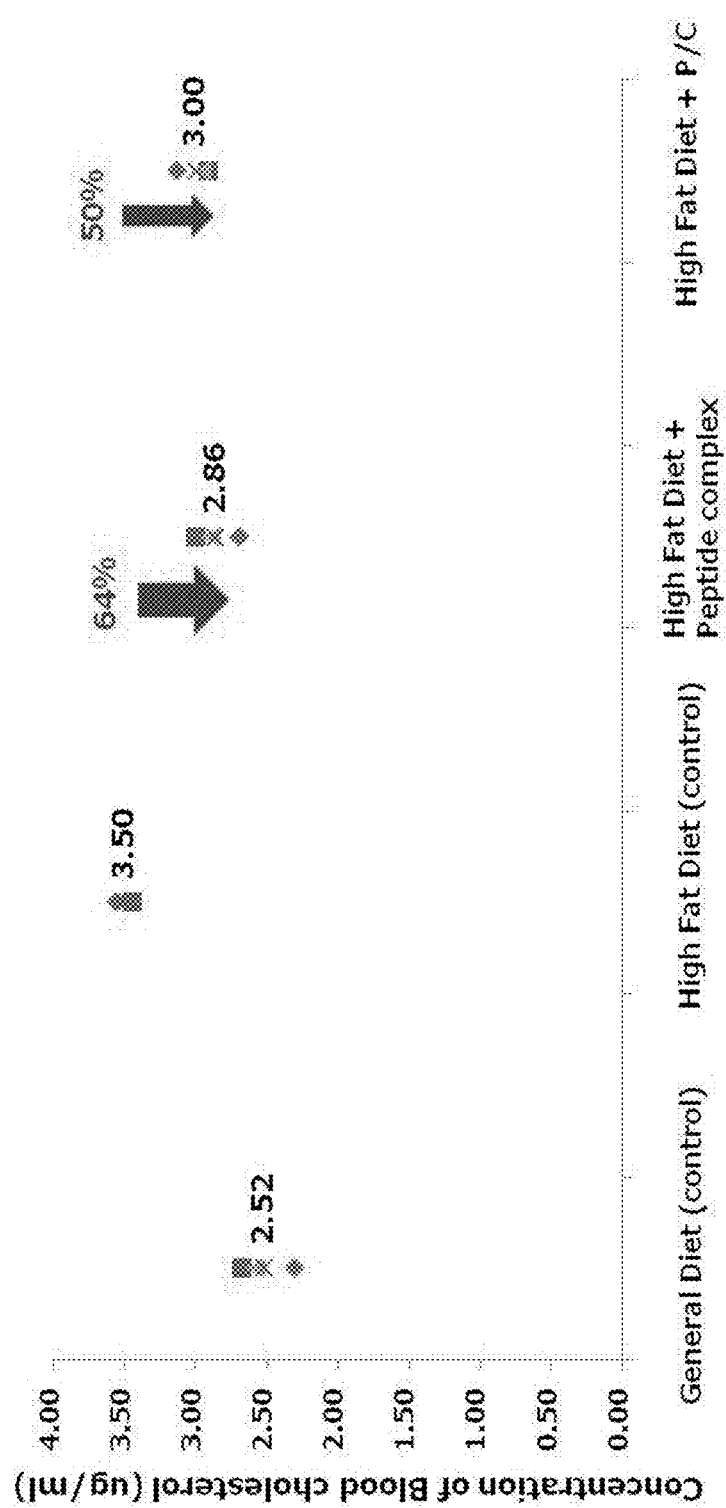
FIG. 18 shows the measured results of cholesterol levels in obtained blood samples, after treatment with the peptide complexes according to the present invention in obese mouse models induced by feeding a high-fat feed to a C57BL/6 mouse model, which is an experimental animal model.

As shown in FIG. 18, it was confirmed that as a result of measuring blood cholesterol levels in the mice after completion of the experiment, the blood cholesterol levels were 2.52 μg/ml in the general diet-fed group, 3.5 μg/ml in the high-fat diet-fed group, and 2.86 μg/ml in the high-fat diets-fed and peptide complex-fed group. It indicates that the peptide complex lowered the elevated cholesterol levels by obesity.

Figure 19:
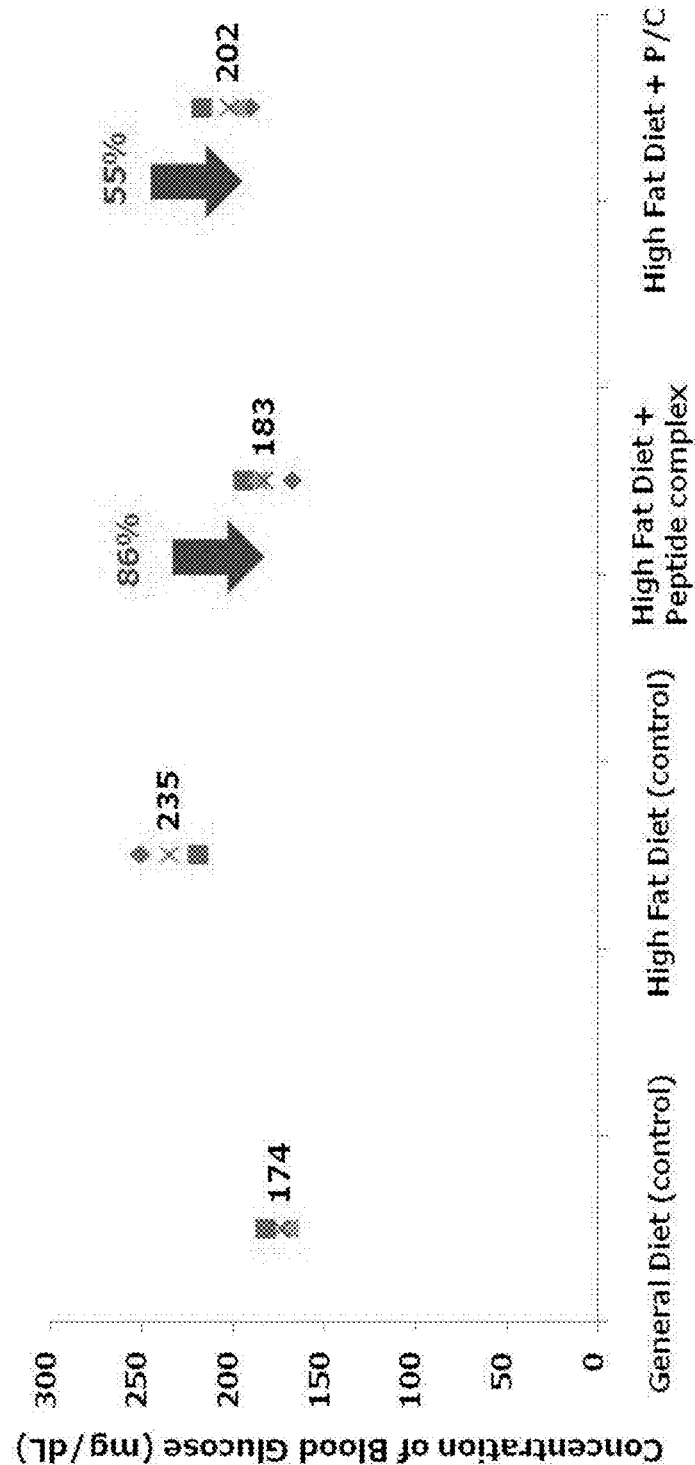
FIG. 19 shows the measured results of blood sugar levels in obtained blood samples, after treatment with the peptide complexes according to the present invention in obese mouse models induced by feeding a high-fat feed to a C57BL/6 mouse model, which is an experimental animal model.

As shown in FIG. 19, it was confirmed that as a result of measuring blood sugar levels after completion of the experiment, the blood sugar levels were 174 mg/dL in mice of the general diet-fed group, and increased to 235 mg/dL in the high-fat diet-fed group, whereas a blood sugar levels were 183 mg/dL in the high-fat diets-fed and peptide complex-fed group and decreased similarly to the the general diet-fed group.

Example 4: Control of Blood Sugar Levels

In this animal experiment, male C57BL/6 (normal mouse) (purchased from Samtako Bio Korea, Co., Ltd.) and C57BLKS/JLepr (diabetes model mouse, db/db mouse) (purchased from Central Lab. Animal Inc.) were used, together with the peptide complex as an anti-diabetic and/or anti-obesity active material, and sitagliptin as a positive control drug.

In this example, the anti-diabetes and/or anti-obesity active complex was evaluated for acute anti-diabetic efficacy (single administration) in a normal mouse model and a genetically potential-diabetic model, using GTT (glucose tolerance test), which is a representative diagnostic method for diabetes.

The environmental condition for housing the mice was maintained at a temperature of 22-24° C. and a relative humidity of 50-30%, with four per cage. In addition, the environmental condition was maintained at an illuminance of 150-300 Lux from 8:00 am to 8:00 pm, and 12 hours lighting and 12 hours lights out per day. The mice were allowed free access to a general diet (18% protein, manufactured in 2018, Harlan Laboratories Inc, USA). The mice were fasted for 4 hours or more before the ITT experiment and for 12 hours or more before the GTT experiment. The complex formulations were orally administered by force with the aid of a disposable oral administration syringe one hour before the GTT experiment. For the GTT experiment, the mice were allowed free access to a high-fat diet at 0 (zero) hour of the experiment. After 40 minutes of free access to a high-fat diet, blood samples were collected from the tail vein at intervals of 0, 30, 60, 90, 120, and 180 minutes to examine the blood glucose levels. Blood samples were measured for blood glucose levels using Accu-Chek active (Roche). On the other hand, sitagliptin, used as a therapeutic agent for diabetes, was selected as a positive control drug and administered at a dose of 100 mg/kg. The complex formulations selected as anti-diabetes and/or anti-obesity active candidates were divided into doses of 100 mg/kg for experimental groups, and four mice were used in each experimental group.

Figure 20:
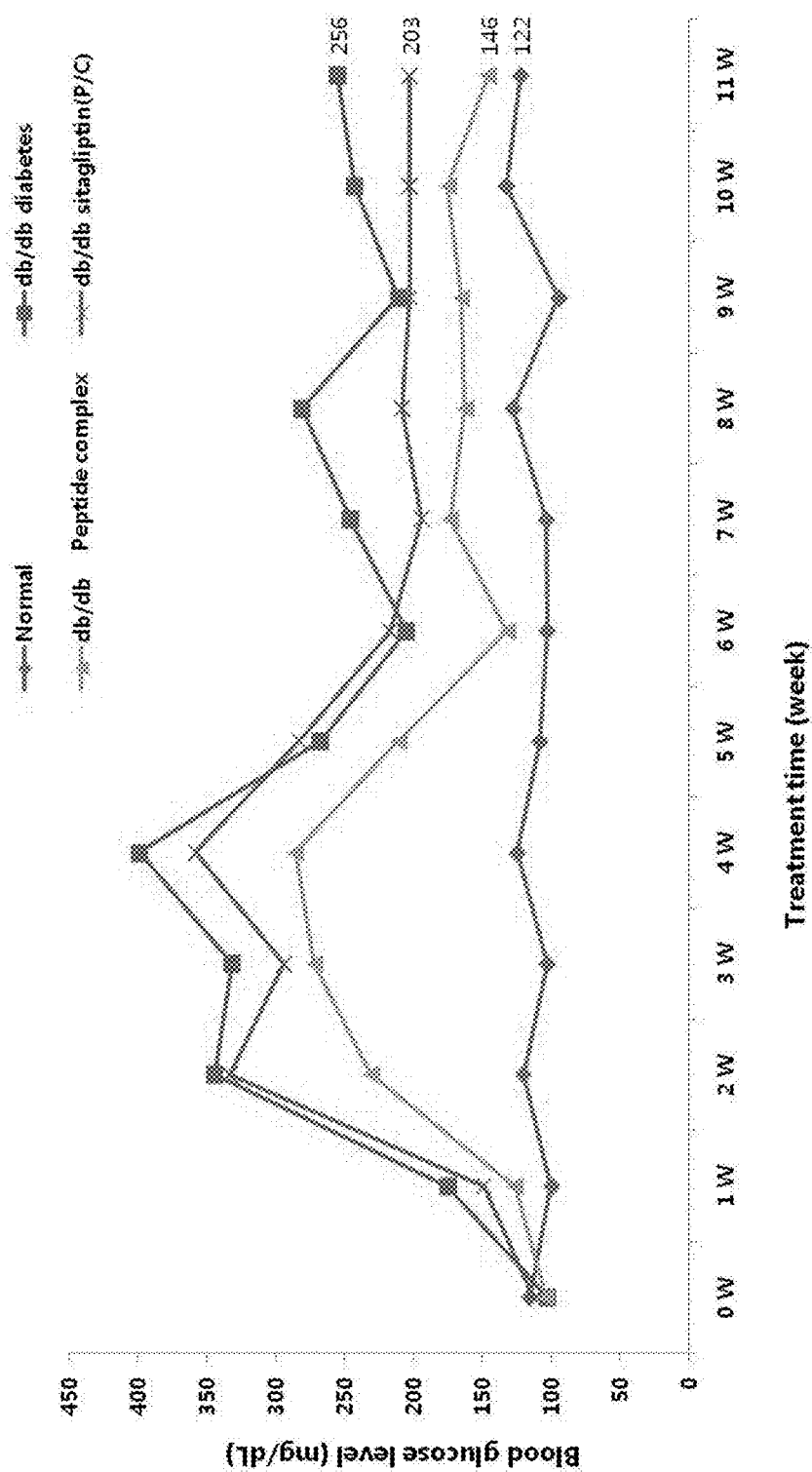
FIG. 20 shows the measured results of changes in blood sugar levels in obtained blood samples, after treatment with the peptide complexes according to the present invention in diabetes-induced db/db mouse models.

As shown in FIG. 20, it was observed that the elevated blood sugar levels by the high-fat diet were reduced after treatment with the peptide complex. In the diabetes-induced mouse models, the high blood sugar levels in the diabetes were decreased.

Figure 21:
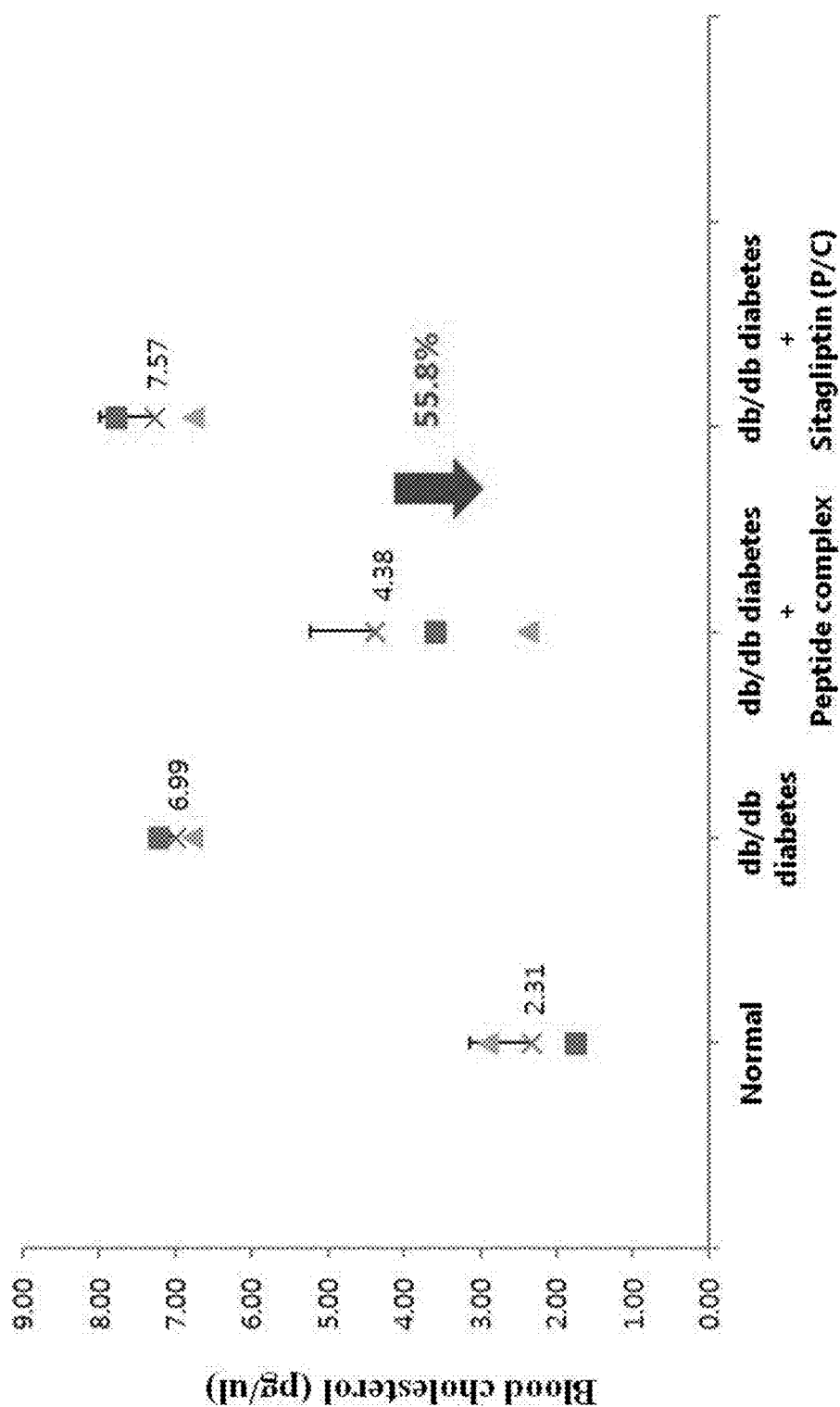
FIG. 21 shows the measured results of changes in cholesterol levels in obtained blood samples, after treatment with the peptide complexes according to the present invention in diabetes-induced db/db mouse models.

As shown in FIG. 21, it was confirmed that the blood cholesterol levels in the both the high-fat diets-fed and peptide complex-fed group were lower than those in the high-fat diet-fed control group.

Figure 22:
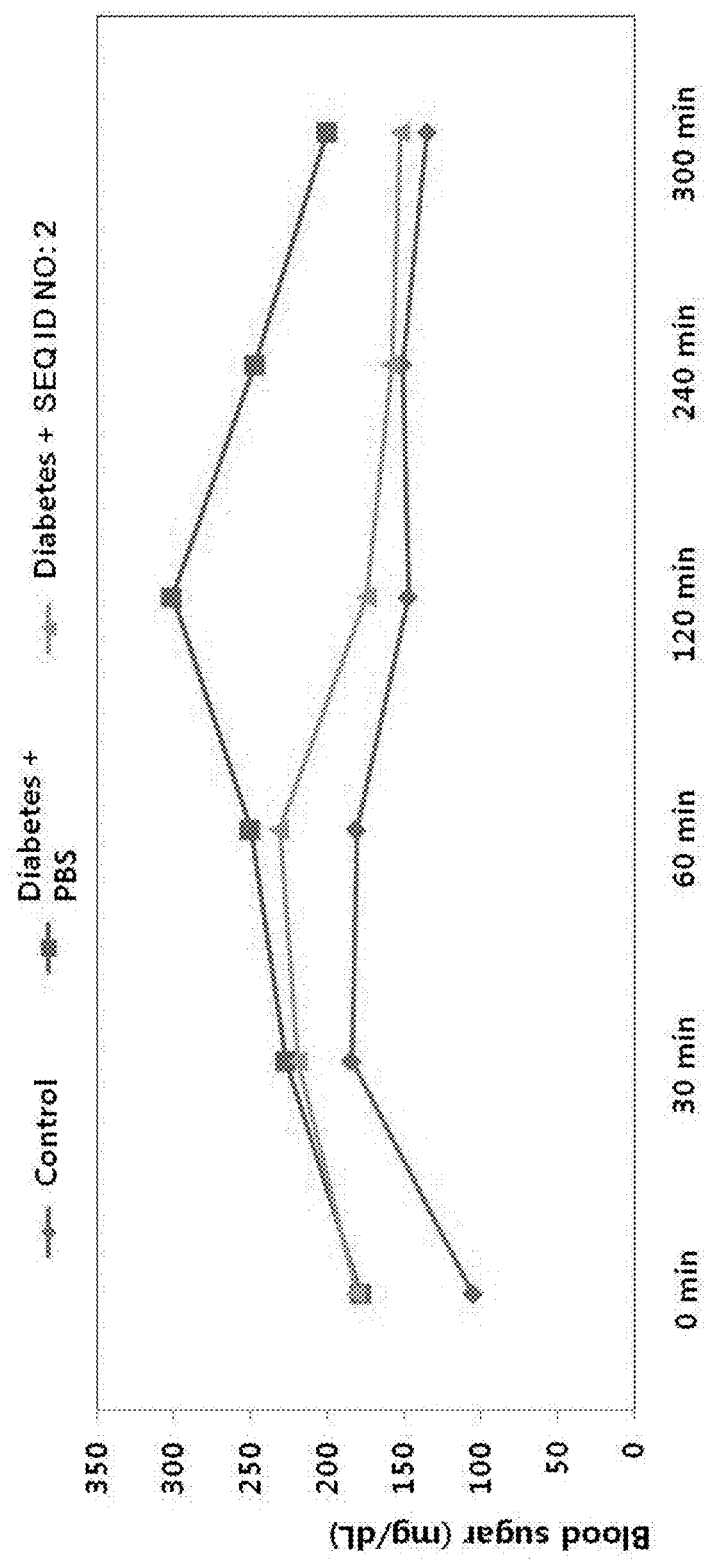
FIG. 22 shows the measured results of changes in blood sugar levels in obtained blood samples, after treatment with the peptide consisting of the amino acid sequence of SEQ ID NO: 2 in diabetes-induced db/db mouse models according to an embodiment of the present invention.
Figure 23:
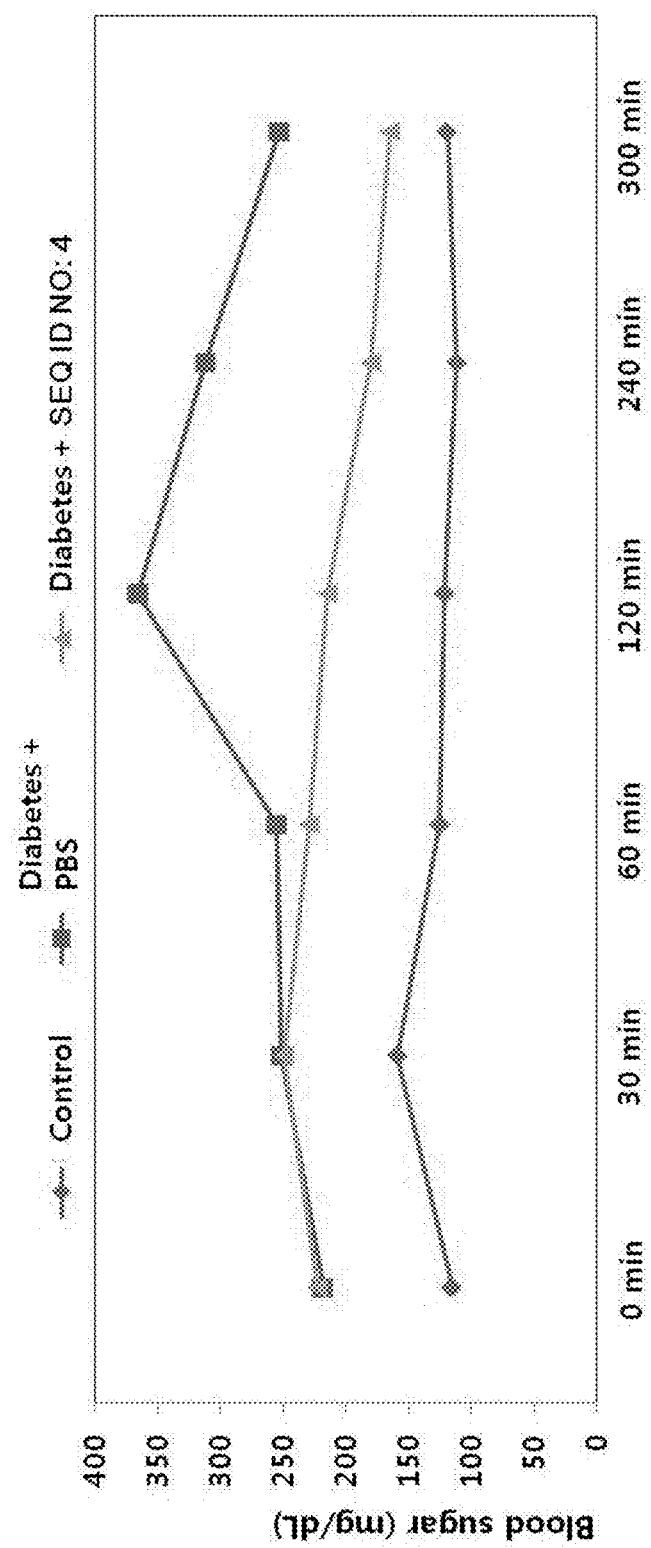
FIG. 23 shows the measured results of changes in blood sugar levels in obtained blood samples, after treatment with the peptide consisting of the amino acid sequence of SEQ ID NO: 4 in diabetes-induced db/db mouse models according to an embodiment of the present invention.

In addition, after starvation for 16 hours, DB/DB diabetes-induced mice were fed for 30 minutes and then administered with the peptides. Blood sugar levels were measured over times and the results are shown in FIGS. 22 and 23 and Tables 7 and 8.

TABLE 7

|  | High-Fat Diabetes | | |
|---|---|---|---|
|  | Normal | PBS | SEQ ID NO: 2 |
| Fasting | 105 | 78 | 181 |
| 30 minutes | 184 | 227 | 219 |
| 60 minutes | 181 | 250 | 231 |
| 120 minutes | 147 | 301 | 174 |
| 240 minutes | 151 | 247 | 158 |
| 300 minutes | 135 | 200 | 152 |

TABLE 8

|  | High-Fat Diabetes | | |
|---|---|---|---|
|  | Normal | PBS | SEQ ID NO: 4 |
| Fasting | 115 | 218 | 222 |
| 30 minutes | 159 | 251 | 249 |
| 60 minutes | 125 | 255 | 229 |
| 120 minutes | 121 | 366 | 215 |
| 240 minutes | 112 | 312 | 180 |
| 300 minutes | 119 | 253 | 165 |

As shown in FIGS. 22 and 23 and Tables 7 and 8, it was observed that the blood sugar levels in the groups treated with the peptide consisting of the amino acid sequence of SEQ ID NO: 2 or SEQ ID NO: 4 were lowered in a time-dependent manner.

Figure 24A:
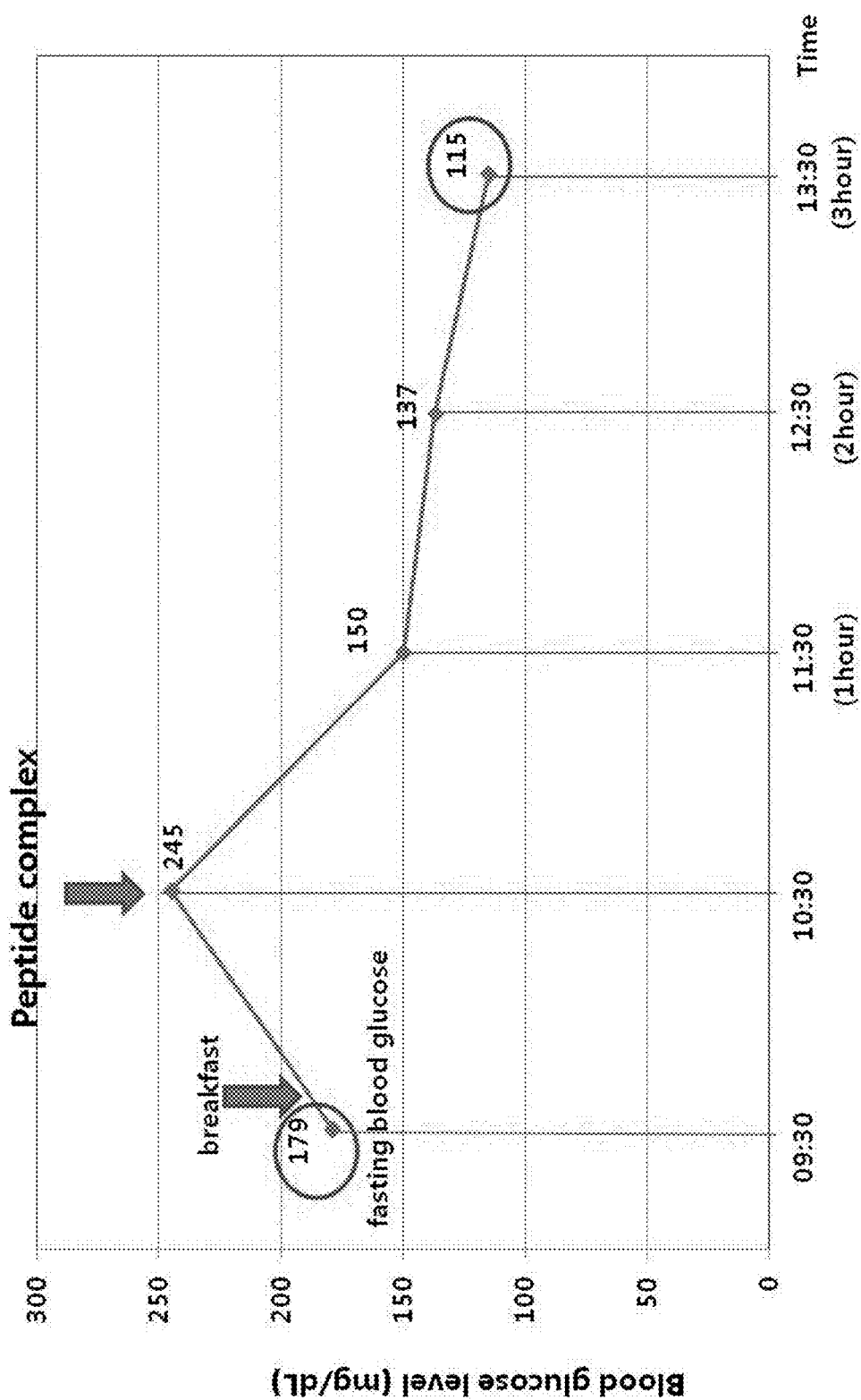
FIGS. 24a to 24d show the measured results of changes in blood sugar levels in obtained blood samples, after treatment with the peptide complexes according to the present invention in diabetic patients having high blood sugar levels according to an embodiment of the present invention.
Figure 24B:
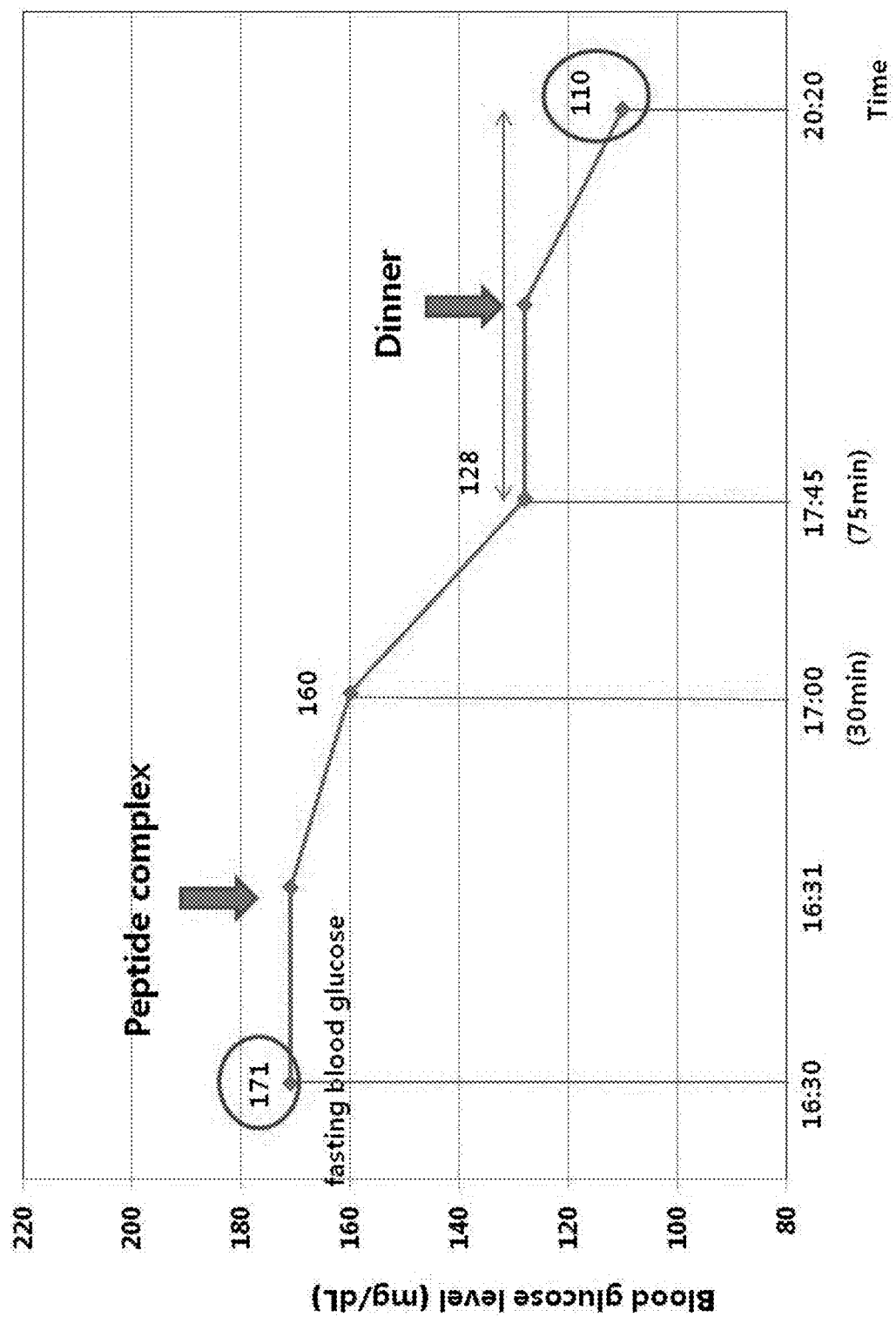
Figure 24C:
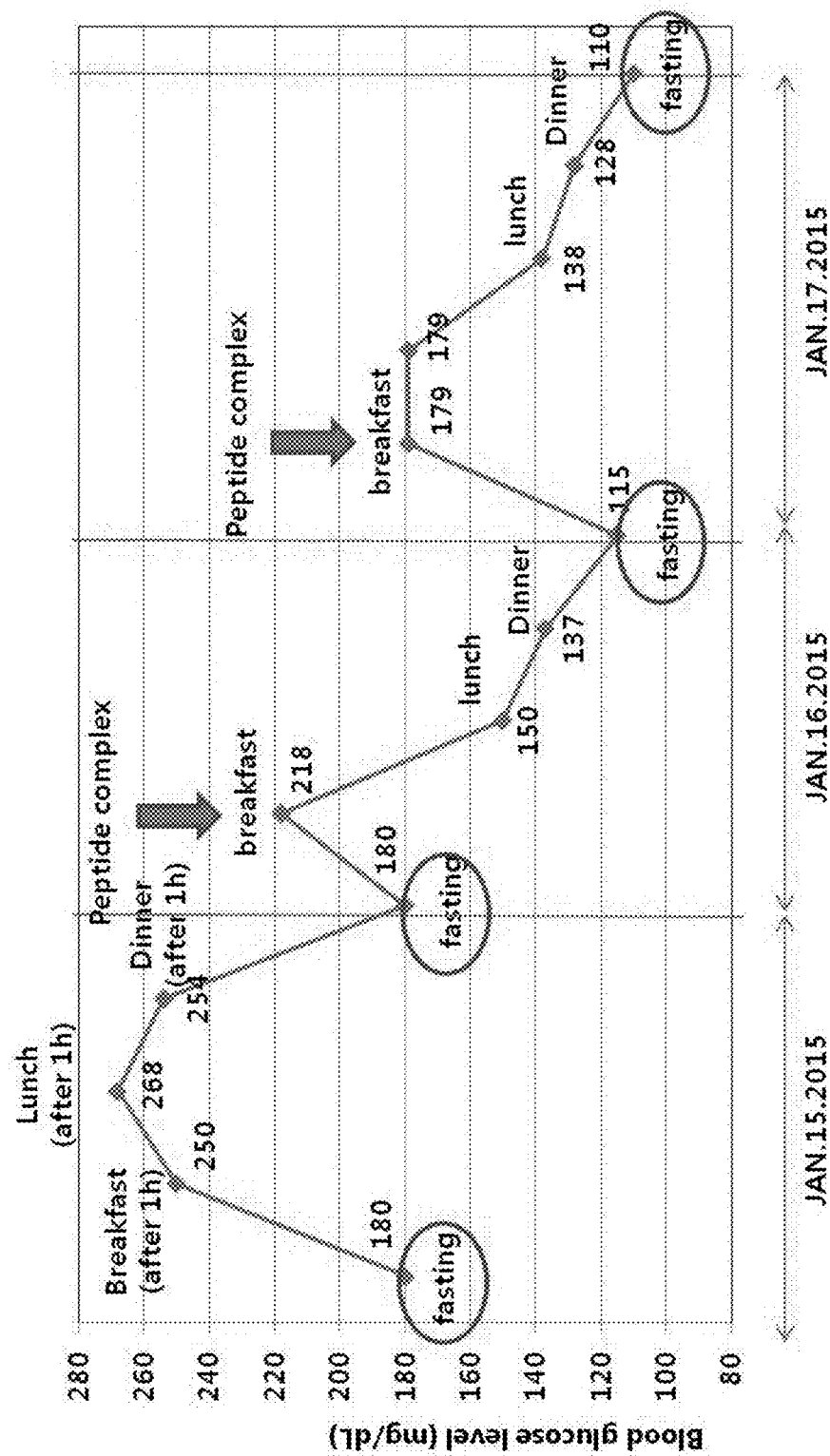
Figure 24D:
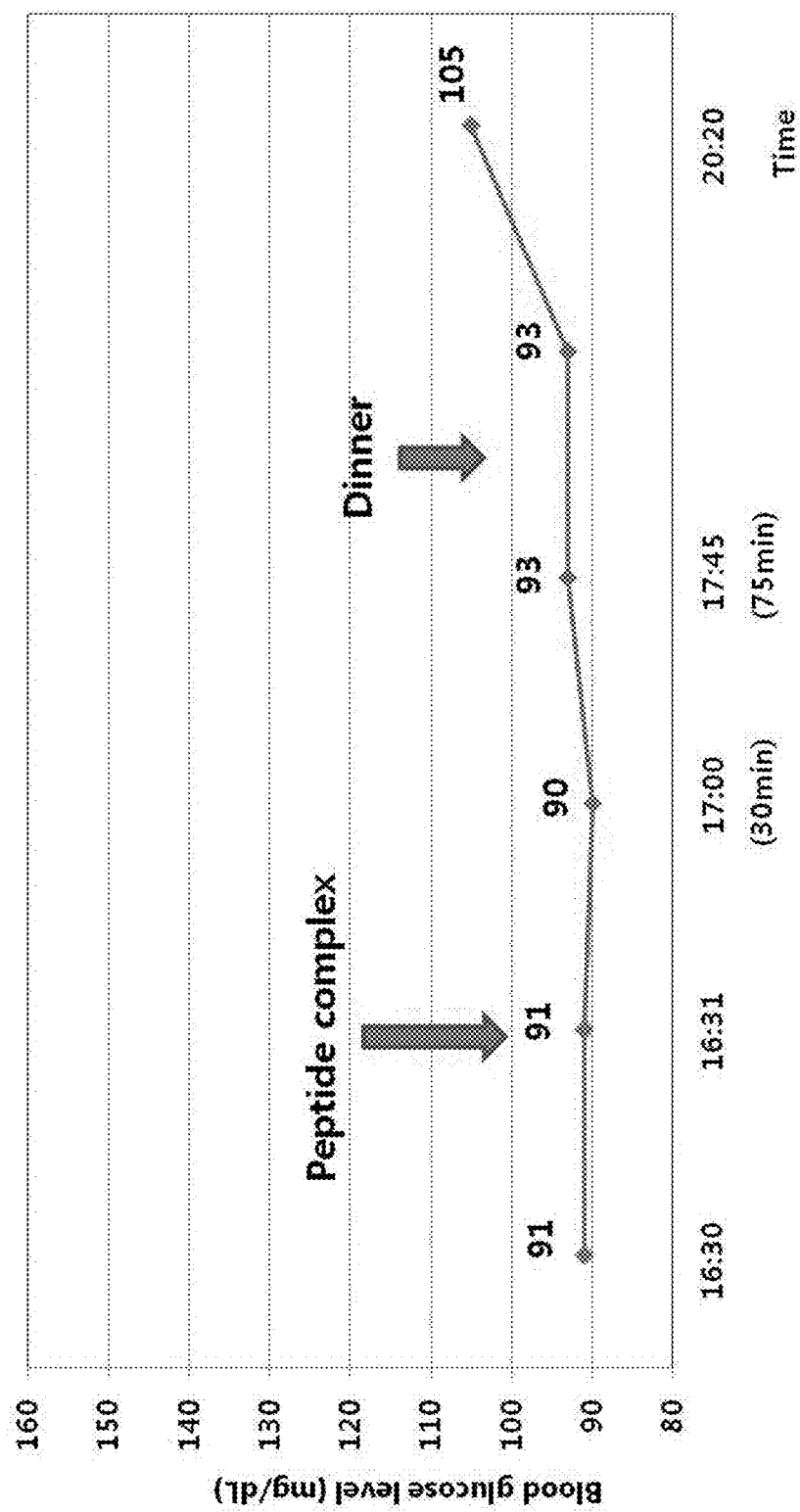

Example 5: Observation of Effect of Reducing Blood Sugar Level Through Clinical Experiment A brief clinical test was performed for subjects aged 45 to 65 years with a fasting blood sugar level of 170 mg/dL or more. They were given a complex formulation 30 minutes after meals. Blood samples were collected from the subjects at intervals of 30, 60, 90, 120, 150, and 180 minutes, and then measured for blood sugar levels using Accu-Chek active (Roche). The results are shown in FIGS. 24a and 24b.

As shown in FIGS. 24a to 24d, it was observed that the blood sugar levels by the complex formulation were decreased in all the tested subjects.

INDUSTRIAL AVAILABILITY

The prevent invention relates to a peptide having anti-obesity and anti-diabetic efficacy and use thereof.

The invention claimed is:

1. A peptide consisting of the amino acid sequence of SEQ ID NO: 4.

2. The peptide according to claim 1, wherein the peptide has anti-obesity or anti-diabetic activity.

3. The peptide according to claim 1, wherein the peptide is coupled with a protecting group selected from the group consisting of an acetyl group, a fluorenylmethoxycarbonyl group, a formyl group, a palmitoyl group, a myristyl group, a stearyl group, and a polyethylene glycol (PEG) at the N-terminal end of the peptide.

4. The peptide according to claim 1, wherein the peptide is coupled with an amino group (—NH$_2$), or an azide group (—NHNH$_2$) at the C-terminal end of the peptide.

5. The peptide according to claim 1, wherein the peptide downregulates the expression of one or more adipogenic markers selected from the group consisting of peroxisome proliferator-activated receptor gamma (PPARγ), acetyl-CoA carboxylase (ACC), and adipose-specific fatty acid-binding protein 2 (aP2).

6. The peptide according to claim 1, wherein the peptide upregulates the expression of one or more lipolytic factors selected from the group consisting of phospho-hormone-sensitive lipase (pHSL), AMP-activated protein kinase α1 (AMPK-α1), comparative gene identification-58 (CGI-58), and adipose triglyceride lipase (ATGL).

7. The peptide according to claim 1, wherein the peptide increases lipolysis.

8. The peptide according to claim 1, wherein the peptide inhibits adipogenesis.

9. The peptide according to claim 1, wherein the peptide lowers blood sugar levels.

10. The peptide according to claim 1, wherein the peptide reduces the size of adipocytes.

11. The peptide according to claim 1, wherein the peptide reduces the levels of cholesterol in blood.

12. A pharmaceutical composition for preventing or treating obesity, comprising the amino acid sequence of SEQ ID NO: 4 as an active ingredient.

13. The pharmaceutical composition according to claim 12, further comprising one or more peptides selected from the group consisting of the peptide consisting of the amino acid sequence selected from the group consisting of SEQ ID NO: 1, SEQ ID NO: 2, SEQ ID NO: 3, SEQ ID NO: 5, SEQ ID NO: 6, and SEQ ID NO: 7.

14. A pharmaceutical composition for preventing or treating diabetes, comprising the peptide consisting of the amino acid sequence of SEQ ID NO: 4 as an active ingredient.

15. The pharmaceutical composition according to claim 14, further comprising one or more peptides selected from the group consisting of the peptide consisting of the amino acid sequence selected from the group consisting of SEQ ID NO: 1, SEQ ID NO: 2, SEQ ID NO: 3, SEQ ID NO: 5, SEQ ID NO: 6, and SEQ ID NO: 7.

* * * * *

SEQUENCE LISTING

```
<160> NUMBER OF SEQ ID NOS: 17

<210> SEQ ID NO 1
<211> LENGTH: 5
<212> TYPE: PRT
<213> ORGANISM: Artificial Sequence
<220> FEATURE:
<223> OTHER INFORMATION: Peptide 1

<400> SEQUENCE: 1

Leu Lys Thr Arg Asn
1               5
```

```
<210> SEQ ID NO 2
<211> LENGTH: 9
<212> TYPE: PRT
<213> ORGANISM: Artificial Sequence
<220> FEATURE:
<223> OTHER INFORMATION: Peptide 2

<400> SEQUENCE: 2

Lys Gly Ala Cys Thr Gly Trp Met Ala
1               5

<210> SEQ ID NO 3
<211> LENGTH: 9
<212> TYPE: PRT
<213> ORGANISM: Artificial Sequence
<220> FEATURE:
<223> OTHER INFORMATION: Peptide 3

<400> SEQUENCE: 3

Lys Gly Ala Ser Thr Gly Trp Met Ala
1               5

<210> SEQ ID NO 4
<211> LENGTH: 10
<212> TYPE: PRT
<213> ORGANISM: Artificial Sequence
<220> FEATURE:
<223> OTHER INFORMATION: Peptide 4

<400> SEQUENCE: 4

Ala Cys Tyr Leu Pro His Pro Trp Phe Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Peptide 5

<400> SEQUENCE: 5

Ala Ser Tyr Leu Pro His Pro Trp Phe Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Peptide 6

<400> SEQUENCE: 6

Cys Asp Leu Arg Arg Leu Glu Met Tyr Cys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Peptide 7

<400> SEQUENCE: 7

Ser Asp Leu Arg Arg Leu Glu Met Tyr Ser
1               5                   10

<210> SEQ ID NO 8
```

```
<211> LENGTH: 20
<212> TYPE: DNA
<213> ORGANISM: Artificial Sequence
<220> FEATURE:
<223> OTHER INFORMATION: PPARgamma F

<400> SEQUENCE: 8
ttttcaaggg tgccagtttc                                              20

<210> SEQ ID NO 9
<211> LENGTH: 20
<212> TYPE: DNA
<213> ORGANISM: Artificial Sequence
<220> FEATURE:
<223> OTHER INFORMATION: PPARgamma R

<400> SEQUENCE: 9
aatccttggc cctctgagat                                              20

<210> SEQ ID NO 10
<211> LENGTH: 24
<212> TYPE: DNA
<213> ORGANISM: Artificial Sequence
<220> FEATURE:
<223> OTHER INFORMATION: ACC F

<400> SEQUENCE: 10
accttactgc catcccatgt gcta                                         24

<210> SEQ ID NO 11
<211> LENGTH: 24
<212> TYPE: DNA
<213> ORGANISM: Artificial Sequence
<220> FEATURE:
<223> OTHER INFORMATION: ACC R

<400> SEQUENCE: 11
gtgcctgatg atcgcacgaa caaa                                         24

<210> SEQ ID NO 12
<211> LENGTH: 20
<212> TYPE: DNA
<213> ORGANISM: Artificial Sequence
<220> FEATURE:
<223> OTHER INFORMATION: aP2 F

<400> SEQUENCE: 12
catcagcgta aatggggatt                                              20

<210> SEQ ID NO 13
<211> LENGTH: 20
<212> TYPE: DNA
<213> ORGANISM: Artificial Sequence
<220> FEATURE:
<223> OTHER INFORMATION: aP2 R

<400> SEQUENCE: 13
acacattcca ccaccagctt                                              20

<210> SEQ ID NO 14
<211> LENGTH: 24
<212> TYPE: DNA
<213> ORGANISM: Artificial Sequence
<220> FEATURE:
<223> OTHER INFORMATION: AMPK-a1 F

<400> SEQUENCE: 14
```

```
tgaccggaca taaagtggct gtga                                          24

<210> SEQ ID NO 15
<211> LENGTH: 24
<212> TYPE: DNA
<213> ORGANISM: Artificial Sequence
<220> FEATURE:
<223> OTHER INFORMATION: AMPK-a1 R

<400> SEQUENCE: 15
tgatgatgtg agggtgcctg aaca                                          24

<210> SEQ ID NO 16
<211> LENGTH: 24
<212> TYPE: DNA
<213> ORGANISM: Artificial Sequence
<220> FEATURE:
<223> OTHER INFORMATION: CGI58 F

<400> SEQUENCE: 16
tgtgcaggac tcttacttgg cagt                                          24

<210> SEQ ID NO 17
<211> LENGTH: 24
<212> TYPE: DNA
<213> ORGANISM: Artificial Sequence
<220> FEATURE:
<223> OTHER INFORMATION: CGI58 R

<400> SEQUENCE: 17
gtttctttgg gcagaccggt ttct                                          24
```